US010545108B2

(12) United States Patent
Samarao et al.

(10) Patent No.: US 10,545,108 B2
(45) Date of Patent: Jan. 28, 2020

(54) NANOSTRUCTURED GAS SENSOR

(71) Applicants: Robert Bosch GmbH, Stuttgart (DE);
Ashwin K. Samarao, Sunnyvale, CA (US); Gary O'Brien, Palo Alto, CA (US); Ando Feyh, Reutlingen (DE)

(72) Inventors: Ashwin K. Samarao, Sunnyvale, CA (US); Gary O'Brien, Palo Alto, CA (US); Ando Feyh, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 164 days.

(21) Appl. No.: 15/539,999

(22) PCT Filed: Dec. 28, 2015

(86) PCT No.: PCT/US2015/067678
§ 371 (c)(1),
(2) Date: Jun. 26, 2017

(87) PCT Pub. No.: WO2016/109430
PCT Pub. Date: Jul. 7, 2016

(65) Prior Publication Data
US 2018/0011043 A1  Jan. 11, 2018

Related U.S. Application Data

(60) Provisional application No. 62/097,491, filed on Dec. 29, 2014, provisional application No. 62/097,465, filed on Dec. 29, 2014.

(51) Int. Cl.
*G01N 33/00*   (2006.01)
*G01N 27/12*   (2006.01)
*H01L 21/02*   (2006.01)

(52) U.S. Cl.
CPC ......... *G01N 27/127* (2013.01); *G01N 33/004* (2013.01); *G01N 33/0047* (2013.01);
(Continued)

(58) Field of Classification Search
CPC .............. G01N 27/127; G01N 33/004; G01N 33/0047; G01N 33/4972
See application file for complete search history.

(56) References Cited

U.S. PATENT DOCUMENTS 4,542,640 A * 9/1985 Clifford ............. G01N 33/0031
422/98
5,528,225 A   6/1996 Sakai et al.
(Continued)

FOREIGN PATENT DOCUMENTS

WO     01/02844 A1   1/2001
WO     03/011747 A1  2/2003

OTHER PUBLICATIONS

Article titled "NO and NO2 Sensing Properties of WO3 and Co3O4 Based Gas Sensors" by Akamatsu et al. and published on Sep. 17, 2013.*

(Continued)

*Primary Examiner* — Blake A Tankersley
(74) *Attorney, Agent, or Firm* — Maginot, Moore & Beck LLP

(57) ABSTRACT

A thin film gas sensor device includes a substrate, a first pillar, a second pillar, a nanostructured thin film layer, and a first and a second electrical contact. The first and second pillars are supported by the substrate. The nanostructured thin film layer is formed with a semi-conductor material including holes. The semiconductor material is configured to undergo a reduction in a density of the holes in the presence of a target gas, thereby increasing an electrical resistance of the nanostructured thin film layer. The first and the second electrical contacts are operably connected to the nanostructured thin film layer, such that the increase in electrical resistance can be detected.

14 Claims, 21 Drawing Sheets

(52) U.S. Cl.
CPC .... *H01L 21/0262* (2013.01); *H01L 21/02565* (2013.01); *H01L 21/02603* (2013.01)

(56) References Cited

U.S. PATENT DOCUMENTS

| | | | |
|---|---|---|---|
| 2004/0163444 A1 | 8/2004 | Dimeo, Jr. et al. | |
| 2012/0247186 A1* | 10/2012 | Sanjeeb | G01N 33/0037 73/31.05 |
| 2014/0109649 A1* | 4/2014 | Fleischer | G01N 27/4143 73/31.02 |
| 2014/0167791 A1 | 6/2014 | Feyh et al. | |
| 2016/0169824 A1* | 6/2016 | Shin | G01N 27/125 73/31.06 |

OTHER PUBLICATIONS

Article titled "CuO Basic Information" by anonymous and retrieved on May 15, 2019 at https://www.pveducation.org/pvcdrom/materials/cuo.*

European Extended Search Report in corresponding EP patent application 15 876 101.5, dated Aug. 2, 2018 (8 pages).

Qingze Jiao et al., "Preparation of Hollow Co3O4 Microspheres and their Ethanol Sensing Properties," Inorganic Chemistry, vol. 51, No. 21, Oct. 8, 2012 (8 pages).

M. E. Donders et al., "Remote Plasma Atomic Layer Deposition of Co3O4 Thin Films," Journal of the Electrochemical Society, vol. 158, No. 4, Mar. 2, 2011 (5 pages).

Ching-Liang Dai et al., "Cobalt Oxide Nanosheet and CNT Micro Carbon Monoxide Sensor Integrated with Readout Circuit on Chip," SENSORS, vol. 10, No. 3, Mar. 2, 2010 (12 pages).

Nalage S R et al., "Novel Method for Fabrication of NiO Sensor for NO2 Monitoring," Journal of Materials Science: Materials in Electronics, vol. 24, No. 1, Aug. 14, 2012 (8 pages).

Peter Antony Premkumar et al., "NiO Thin Films Synthesized by Atomic Layer Deposition using Ni(dmamb)2 and Ozone as Precursors," Chemical Vapor Deposition, vol. 18, No. 1-3, Mar. 5, 2012 (9 pages).

International Search Report corresponding to PCT Application No. PCT/US2015/067678, dated Apr. 14, 2016 (4 pages).

Soleimanpour, Amir Masoud; Synthesis, fabrication and surface modification of nanocrystalline nickel oxide for electronic gas sensors; The University of Toledo Digital Repository, Theses and Dissertations; May 2013, also available at http://utdr.utoledo.edu/theses-dissertations/212/ (144 pages).

* cited by examiner

Variation of the optical transmittance of $60SiO_2 \cdot 40NiO$ at $\lambda = 650$ nm for films heat-treated at 500°C and exposed to 1 vol% CO in air at four different testing temperatures.

Response-recovery characteristics for $Co_3O_4$ nanowires and bulk $Co_3O_4$ sensors to $C_2H_5OH$ gas operated at 350°C. The $C_2H_5OH$ gas concentration is fixed at 300 ppm.

Gas-sensing transients of (a) $Co_3O_4$ nanosheets, (b) $Co_3O_4$ nanorods, and (c) $Co_3O_4$ nanocubes to 100 ppm $C_2H_5OH$, 100 ppm $H_2$, 100 ppm CO and 1 ppm $NO_2$ at 300 °C. The nanosheets, nanorods, and nanocubes were prepared by HT of CL-18, CO-1 CLO-18 precursors at 400 °C for 1 h, respectively.

(a) Ninety percent response time ($\tau_{90\%\text{-resp}}$) and (b) 90% recovery time ($\tau_{90\%\text{-rec}}$) of the nanosheets, nanorods, nanocubes, and agglomerated powders of the $Co_3O_4$ specimens at 400 °C.

Gas response ($R_a/R_g$) to 100 ppm $C_2H_5OH$, 100 ppm $H_2$ and 100 ppm CO at 400 °C and the selectivity to $C_2H_5OH$ ($S_{ethanol}/S_{gas}$, $S_{ethanol}$ and $S_{gas}$: gas responses to $C_2H_5OH$ and other gases, respectively): (a) and (e) $Co_3O_4$ nanosheets; (b) and (f) $Co_3O_4$ nanorods; (c) and (g) $Co_3O_4$ nanocubes; and (d) and (h) $Co_3O_4$ agglomerated powders.

NANOSTRUCTURED GAS SENSOR

This application is a 35 U.S.C. § 371 National Stage Application of PCT/US2015/067678, filed on Dec. 28, 2015, which claims the benefit of priority of U.S. provisional application Ser. No. 62/097,465, filed on Dec. 29, 2014, and U.S. provisional application Ser. No. 62/097,491, filed on Dec. 29, 2014, the disclosures of which are herein incorporated by reference in their entirety.

FIELD

This disclosure relates generally to sensor devices and particularly to thin-film gas sensor devices.

BACKGROUND

Semiconductor gas sensors are used to detect the presence of a particular gas or gasses in an environment to which the sensor is exposed. A common type of gas sensor is a metal oxide semiconductor (MOS) gas sensor. MOS gas sensors, which are also referred to as "thick-film" gas sensors, typically include a heating element and a gas-sensitive portion located between two electrodes. The heating element is activated to heat the gas-sensitive portion to a temperature that is suitable for detecting a target gas. The gas-sensitive portion is a polycrystalline thick-film that is configured to undergo a change in optical transmittance, electrical conduction, and/or ionic conduction in the presence of the target gas. The change of the gas-sensitive portion is detected by an external circuit that is electrically connected to the gas sensor.

Two common types of thick film MOS gas sensors are carbon monoxide sensors and alcohol sensors. Carbon monoxide sensors are used in both automotive and home applications. For example, carbon monoxide sensors are useful for determining the presence, absence, or concentration of carbon monoxide in automotive exhaust products. Carbon monoxide sensors are used in the home for detecting unsafe levels of carbon monoxide. Alcohol sensors are used in applications including automotive fuel systems and breath analyzer devices. In most applications, it is desirable for both types of sensors to be small, inexpensive, accurate, and electrically efficient. It is also desirable for the sensors to quickly determine the concentration of gas in the selected environment.

FIGS. 1 and 2 show part of a gas-sensitive portion 10 of a prior art MOS gas sensor. The polycrystalline material of the gas-sensitive portion 10 includes numerous grains 20. The region of contact between the grains 20 is referred to herein as a grain boundary 22. The grain boundaries 22 are target sites to which molecules of the target gas bind through a process referred to as adsorption. When adsorption of the target gas occurs, the gas-sensitive portion 10 undergoes the above-described change that is detected by the external circuit.

Chemisorption is one type of adsorption that may occur at the grain boundaries 22 in the presence of the target gas. To illustrate the effects of chemisorption, FIG. 1 includes a graph showing an electrical potential barrier at the grain boundary 22 in an environment of air containing oxygen molecules. For an electron 30 to move through the grain boundary 22, it requires enough energy to overcome the potential barrier, which defines a reference magnitude measured in electronvolts (eV). A combination of the potential barriers of all/most of the grain boundaries 22 in the gas-sensitive portion 10 contributes to an electrical resistance of the gas-sensitive portion.

In FIG. 2, the exemplary grain boundary 22 is shown in the presence of molecules of a reducing gas. Chemisorption of the reducing gas has caused a reduction in the magnitude of the potential barrier due to donor electrons from the reducing gas. When the potential barriers are combined, the overall electrical resistance of the gas-sensitive portion 10 is reduced due to the reduction in the magnitude of at least some of the potential barriers at the grain boundaries 22 at which reduction has occurred. The exemplary reduction in electrical resistance of the gas-sensitive portion 10 is detectable by the external circuit connected to the gas sensor as being indicative of the presence of a target gas. Although not shown, in the presence of an oxidizing gas, the magnitude of the potential barrier increases, thereby resulting in an increase in the electrical resistance of the gas-sensitive portion 10, which is also detectable by the external circuit connected to the gas sensor as being indicative of the presence of a target gas.

Heterogeneous catalysis is another process that may occur at the grain boundaries 22, depending on the type gas near the gas-sensitive portion 10. One example of heterogeneous catalysis, referred to as carbon monoxide (CO) oxidation, results in the oxidation of a carbon dioxide ($CO_2$) molecule, due to the presence of a carbon monoxide molecule and an oxygen molecule located near one of the grain boundaries 22 of the gas-sensitive portion 10. Heterogeneous catalysis, in at least some instances, results in the change of the gas-sensitive portion 10, which is detectable by the external circuit connected to the gas sensor as being indicative of the presence of a target gas.

The change in optical transmittance of a thick film MOS gas sensor in the presence of the target gas is also a catalytic reaction. Optical thick film gas sensors are found, for example, in carbon monoxide detectors and typically include an optical gas sensor and a read out circuit. The gas sensor includes a gas sensitive portion formed from a thick film of tin dioxide and nickel oxide, for example, that has been heat treated (annealed) at approximately 500° C. The read out circuit is a circuit that is configured to heat the thick film to an operating temperature and to monitor the optical transmittance of the heated thick film, which varies based on the concentration of carbon monoxide in the environment to which the detector is exposed. As shown in FIG. 3, at the four illustrated operating temperatures, the optical transmittance of the thick film at a wavelength of 650 nm steps to a peak value between approximately two hundred to four hundred seconds after being exposed to an environment having 1 vol % carbon monoxide in air.

When the heating element of the typical MOS gas sensor is activated, other portions of the gas sensor are heated in addition to the gas-sensitive portion. For example, if an intermediary layer is located between the heating element and the gas-sensitive portion, then the heating element heats the intermediary layer in addition to heating the gas-sensitive portion. Furthermore, if the heating element is positioned in contact with or in proximity to a base layer, a substrate layer, or a handle layer, then heat energy from the heating element may undesirably/unnecessarily be transferred thereto. Additionally, since the gas-sensitive portion of a MOS gas sensor is a "thick-film," heating of the gas-sensitive portion has an associated time constant that may be of longer duration than desired. Accordingly, in the typical MOS gas sensor, energy consumed by the heating element is used to heat portions of the gas sensor that are not desired to be heated, and heating the gas-sensitive portion may consume more time than desired.

Thick film MOS gas sensors are useful for sensing a target gas, but are difficult and time consuming to fabricate, especially when the gas sensitive portion includes multiple layers of mutually catalytic materials. Additionally, thick film MOS gas sensors, especially optical-based MOS gas sensors, are larger and slower than is suitable for some applications, such as sensing the presence alcohol. Furthermore, thick film MOS gas sensors consume significant electrical power when being heated to an operating temperature. Therefore, for at least some of the above-described reasons, further developments in the area of gas sensors are desirable.

SUMMARY

According to an exemplary embodiment of the disclosure, a thin film gas sensor device includes a substrate, a first pillar, a second pillar, a nanostructured thin film layer, and a first and a second electrical contact. The first pillar is supported by the substrate, and the second pillar is supported by the substrate. The nanostructured thin film layer is formed with a semi-conductor material including holes. The semiconductor material is configured to undergo a reduction in a density of the holes in the presence of a target gas, thereby increasing an electrical resistance of the nanostructured thin film layer. The first and the second electrical contacts are operably connected to the nanostructured thin film layer such that the increase in electrical resistance can be detected.

In one embodiment, the nanostructured thin film layer is formed from nanostructured nickel oxide (NiO), and the target gas is carbon monoxide.

In another embodiment, the nanostructured thin film layer is formed from nanostructured cobalt oxide ($Co_3O_4$), and the target gas is an alcohol.

In a further embodiment, the nanostructured thin film layer is supported by the first and the second pillars.

In one embodiment, the nanostructured thin film layer is formed using atomic layer deposition.

In another embodiment, the thin film gas sensor device further comprises a third pillar supported by the substrate, a fourth pillar supported by the substrate, and a heater layer supported by the third and the fourth pillars and configured to joule heat the nanostructured thin film layer to a predetermined operating temperature. The nanostructured thin film layer is supported by the first and the second pillars.

In yet another embodiment, the nanostructured thin film layer is formed from nanostructured nickel oxide (NiO), and the predetermined operating temperature is 330° C.

In a further embodiment, the nanostructured thin film layer is formed from nanostructured cobalt oxide ($Co_3O_4$), and the predetermined operating temperature is 400° C.

In one embodiment, a suspended portion of the nanostructured thin film layer is suspended above the substrate.

According to another exemplary embodiment of the disclosure, a method of fabricating a thin film gas sensor device comprises providing a substrate, supporting a first pillar with the substrate, supporting a second pillar with the substrate, and forming a nanostructured thin film layer using a semi-conductor material including holes. The semiconductor material is configured to undergo a reduction in a density of the holes in the presence of a target gas, thereby increasing an electrical resistance of the nanostructured thin film layer. The method further comprises operably connecting a first and a second electrical contact to the nanostructured thin film layer such that the increase in electrical resistance can be detected.

In one embodiment, the method further comprises forming the nanostructured thin film layer from nickel oxide (NiO) using atomic layer deposition.

In another embodiment, the method further comprises forming the nanostructured thin film layer from cobalt oxide ($Co_3O_4$) using atomic layer deposition.

In yet another embodiment, the method further comprises forming a sacrificial layer above the substrate, forming a seed layer from a first material above the substrate, and forming the nanostructured thin film layer from a second material on the seed layer. The method further comprises removing the sacrificial layer to suspend a suspended portion of the seed layer and the nanostructured thin film layer above the substrate.

According to yet another exemplary embodiment of the disclosure, a method of using a thin film gas sensor device comprises obtaining a first electrical resistance reading across a nanostructured thin film layer. The nanostructured thin film layer includes a semi-conductor material including holes, and the semiconductor material is configured to undergo a reduction in a density of the holes in the presence of a target gas, thereby increasing an electrical resistance of the nanostructured thin film layer. The method further comprises exposing the nanostructured thin film layer to a gaseous environment after obtaining the first reading, obtaining a second electrical resistance reading across the nanostructured thin film layer after exposing the nanostructured thin film layer to the gaseous environment, comparing the first obtained reading and the second obtained reading, and determining if the target gas is present in the gaseous environment based upon the comparison of the first obtained reading and the second obtained reading.

In one embodiment, the first and second electrical resistance readings are obtained with the nanostructured thin film layer at a first temperature, and the method further comprises establishing the nanostructured thin film layer at a second temperature prior to exposing the nanostructured thin film layer to the gaseous environment. The second temperature is different from the first temperature. The method further includes obtaining a third electrical resistance reading across the nanostructured thin film layer with the nanostructured thin film layer at the second temperature prior to exposing the nanostructured thin film layer to the gaseous environment, obtaining a fourth electrical resistance reading across the nanostructured thin film layer with the nanostructured thin film layer at the second temperature after exposing the nanostructured thin film layer to the gaseous environment, and comparing the third obtained reading and the fourth obtained reading. Determining if the target gas is present comprises determining if the target gas is present in the gaseous environment based upon the comparison of the first obtained reading, the second obtained reading, the third obtained reading, and the fourth obtained reading.

In another embodiment, the nanostructured thin film layer is formed from nickel oxide (NiO) using atomic layer deposition, and the second operating temperature is 330° C.

In a further embodiment, the nanostructured thin film layer is formed from cobalt oxide ($Co_3O_4$) using atomic layer deposition, and the second operating temperature is 400° C.

BRIEF DESCRIPTION OF THE FIGURES

The above-described features and advantages, as well as others, should become more readily apparent to those of ordinary skill in the art by reference to the following detailed description and the accompanying figures in which:

FIG. 8 is a cross sectional view taken along a line similar to the line V-V of FIG. 4, showing an insulator layer formed on the sacrificial layer and in the trench of the sacrificial layer;

DETAILED DESCRIPTION

Figure 1:
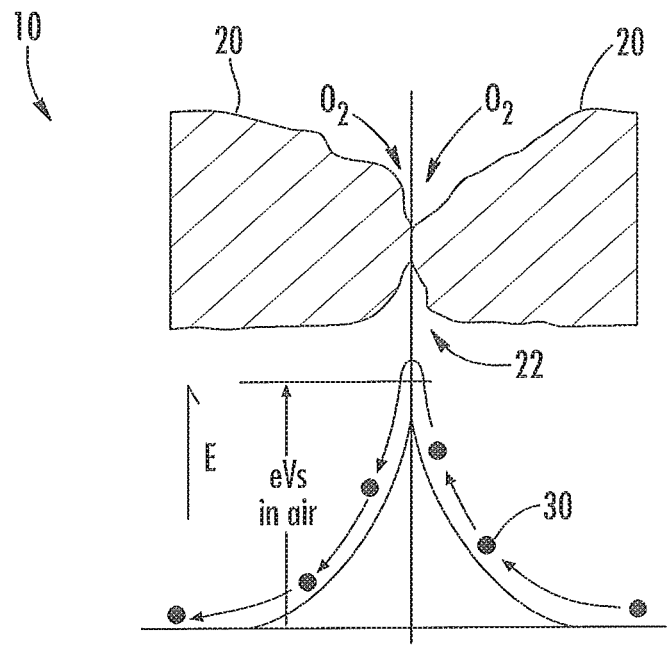
FIG. 1 is a cross sectional view of a grain boundary of a gas-sensitive layer of a prior art thick film MOS gas sensor in an environment of air, and a graph showing a corresponding potential barrier of the grain boundary.
Figure 2:
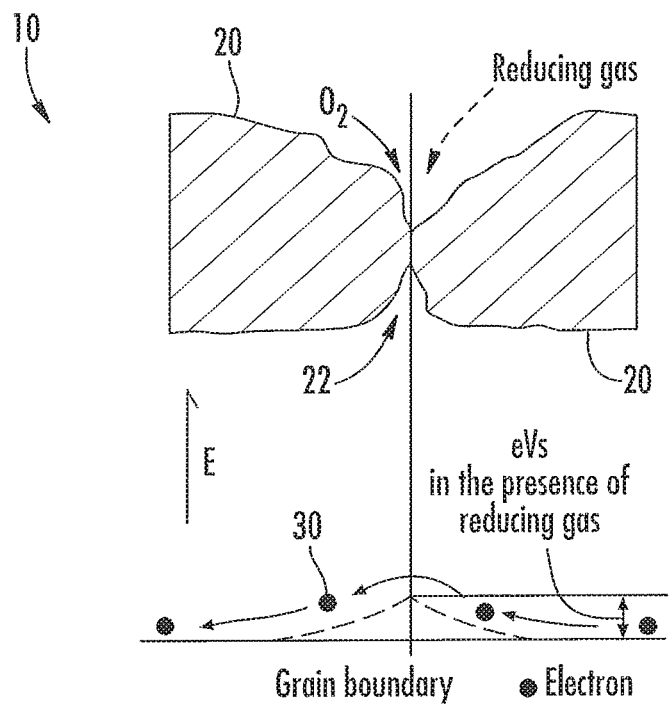
FIG. 2 is a cross sectional view of the grain boundary of FIG. 1 in an environment of air and a reducing gas, and a graph showing a corresponding potential barrier of the grain boundary.
Figure 3:
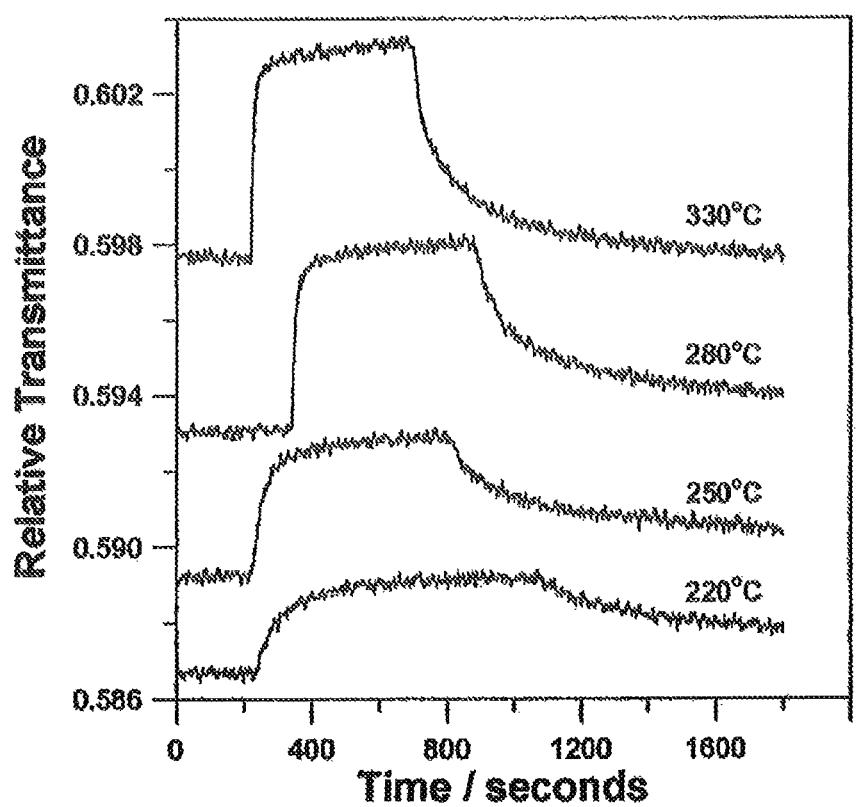
FIG. 3 is a graph showing the relative optical transmittance versus time of a prior art thick film optical-based gas sensor configured to detect carbon monoxide.

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

Figure 4:
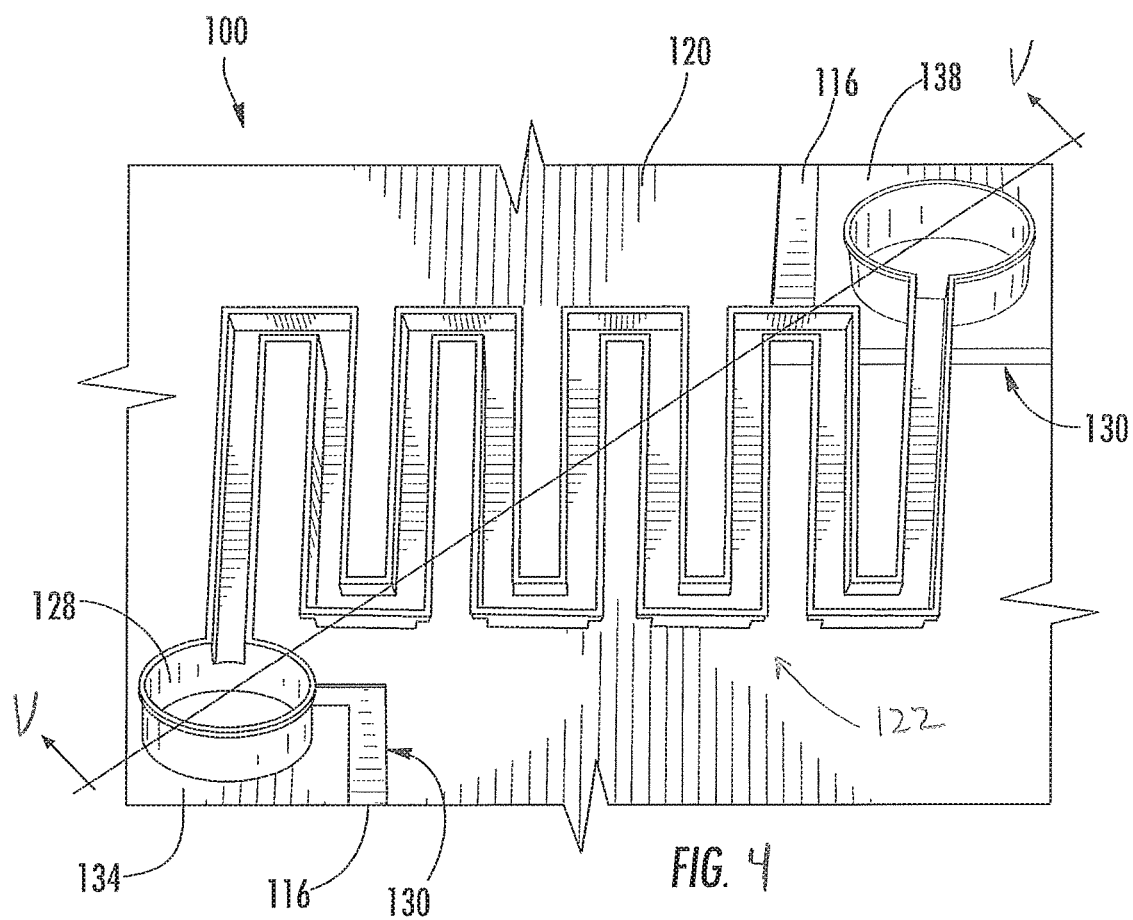
FIG. 4 is perspective view of a thin film gas sensor device, as described herein, the sensor device includes a thin-film heater and gas-sensitive portion defining a serpentine structure having nine legs.
Figure 5:
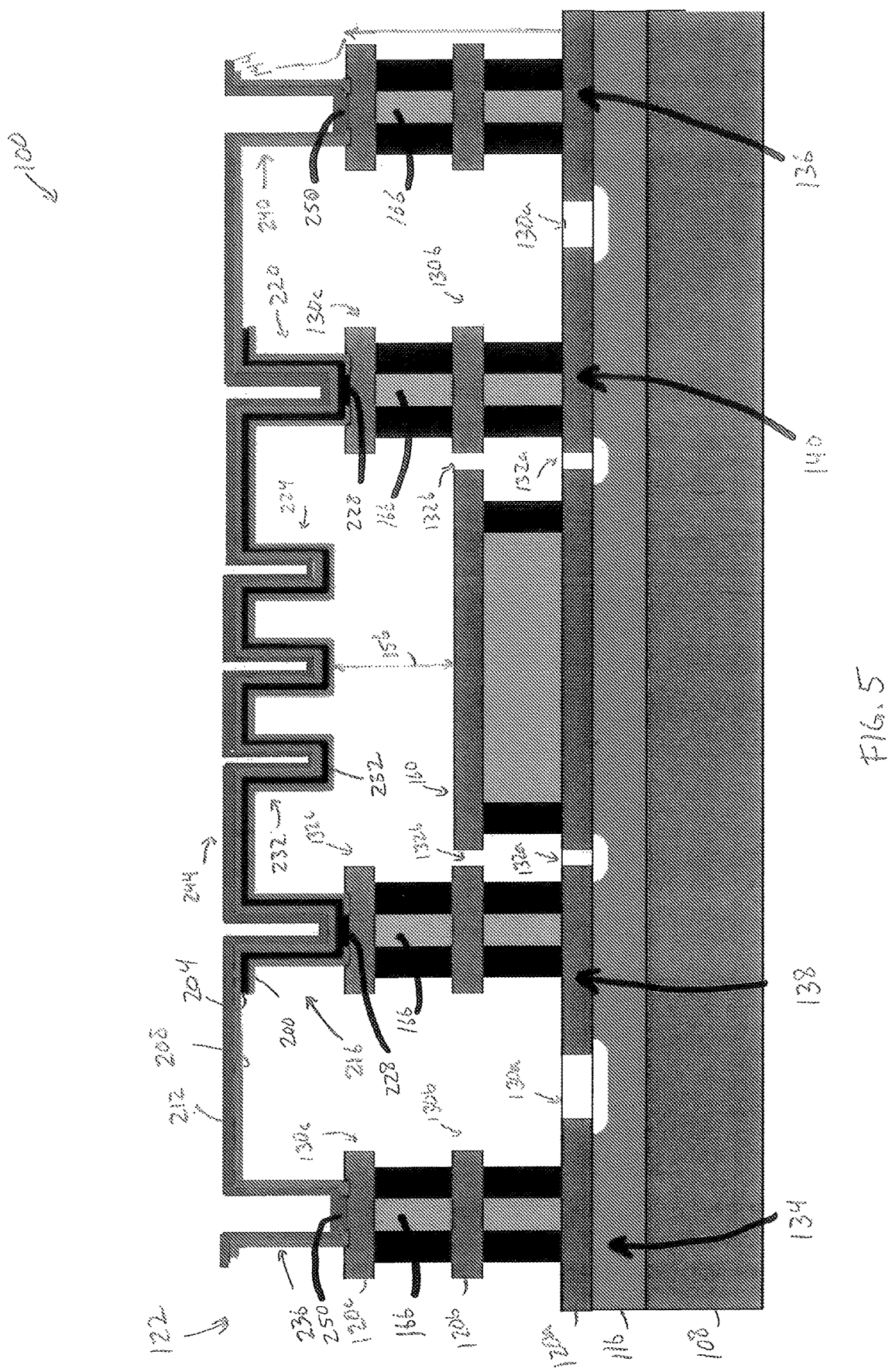
FIG. 5 is a cross sectional view of a sensor device that is substantially identical to the sensor device of FIG. 4, but that includes fewer legs in the serpentine portion of the device, the view of FIG. 5 is taken along a line similar to line V-V of FIG. 4.

As shown in FIGS. 4 and 5, a semiconductor sensor assembly, which in this embodiment is a thin film gas sensor device 100 configured to detect a target gas, such as carbon monoxide or alcohol. The gas sensor device 100 is a non-optical sensor configured to exhibit a change in resistance in the presence of the target gas that is sensed by an external read out circuit (not shown) to detect the presence of the target gas in the environment to which the sensor device 100 is exposed. The gas sensor device 100 has an extremely small form factor making it usable in a wide variety of applications. The exemplary embodiment of the sensor device 100 includes a substrate 108 (FIG. 5), an insulator layer 116, electrically conductive layers 120a, 120b, 120c, and a suspended sensor portion 122.

The substrate 108 is formed from silicon or another desired type of substrate.

The insulator layer 116, in one embodiment, is a deposited dielectric such as, silicon dioxide ($SiO_2$). The insulator layer 116 is deposited over the substrate 108. In another embodiment, the insulator layer 116 is formed from any suitable electrically insulating material.

The electrically conductive layers 120a, 120b, 120c are formed over the insulator layer 116. In one embodiment, the conductive layers 120a, 120b, 120c are formed from platinum (Pt). Openings 130a, 130b, 130c in the conductive layers 120a, 120b, 120c electrically isolate a left sensor pillar 134 and a right sensor pillar 136. Openings 132a, 132b, 132c and the openings 130a, 130b, 130c isolate a left heater pillar 138 and a right heater pillar 140.

The pillars 134, 136, 138, 140 are supported by the substrate 108 and each pollar defines a height that is configured to space the sensor portion 122 a first predetermined distance 144 from the conductive layer 120a and a second predetermined distance 156 from a table structure 160 located between the heater pillars 138, 140. In some embodiments, the sensor device 100 does not include the table structure 160.

The pillars 134, 136, 138, 140 are formed from any desired number of conductive layers 120 that results in the desired predetermined distances 144, 156. A respective conductive path 166 extends through each pillar 134, 136, 138, 140 in order to electrically connect the conductive layers 120a and 120c of each respective pillar.

The sensor portion 122 is formed from four thin films including an insulator layer 200, a heater layer 204, a seed layer 208, and a gas sensitive layer 212. The insulator layer 200 extends from the heater pillar 138 to the heater pillar 140 and defines a left base portion 216, a right base portion 220, and a serpentine portion 224 extending from the left support portion 216 to the right support portion 220. The base portions 216, 220 are formed on the conductive layer 120c and are configured to mechanically support the suspended serpentine portion 224. The serpentine portion 224 defines a substantially U-shaped trench in cross section that provides mechanical stability to the sensor portion 122 and also increases the available surface area for detecting a target gas. In one embodiment, the insulator layer 200 is formed from alumina. In other embodiments, the insulator layer 200 is formed from any suitable electrically insulative material that is configured to be deposited into a thin film using atomic layer deposition (ALD). In yet another embodiment, the sensor portion 122 does not include the insulator layer 200.

The heater layer 204 includes two contact portions 228 and a serpentine portion 232 configured to extend from the heater pillar 138 to the heater pillar 140. The heater layer 204 is supported by the pillars 138, 140. The contact portions 228 are formed on the conductive layer 120c and are configured to electrically connect the heater layer 204 to the heater pillars 138, 140, such that electrical energy is configured to flow from the heater pillars 138, 140 through the serpentine portion 232. The shape of the heater layer 204 corresponds to the shape of the insulator layer 232; accordingly, the serpentine portion 232 defines a substantially U-shaped trench in cross section that may provide further mechanical stability to the sensor portion 122. In one embodiment, the heater layer 204 is formed from platinum. In other embodiments, the heater layer 204 is formed from any suitable electrically conductive material that is configured to be deposited into a thin film using ALD. In the illustrated embodiment, the heater layer 204 is prevented from extending from the heater pillar 138 to the sensor pillar 134 and from the heater pillar 140 to the sensor pillar 136.

The seed layer 208 extends from the sensor pillar 134 to the sensor pillar 136 and defines a left base portion 236, a right base portion 240, and a serpentine portion 244 extending from the left base portion 216 to the right base portion 220. The base portions 216, 220 are formed on the conductive layer 120c and are configured to mechanically support the suspended serpentine portion 244. The seed layer 208 corresponds to the shape of the heater layer 204; accordingly, the serpentine portion 244 defines a substantially U-shaped trench in cross section that may provide further mechanical stability to the sensor portion 122. In one embodiment, the seed layer 208 is formed from alumina or aluminum oxide ($Al_2O_3$). In other embodiments, the seed layer 208 is formed from any suitable electrically insulative material that is configured to be deposited into a thin film using atomic layer deposition (ALD). Additionally, the selection of the seed layer 208 is based on the desired porosity of the sensor layer 212, as described below.

The gas-sensitive layer 212 (also referred to herein as a sensor layer and a nanostructured thin film layer) is a thin-film that is formed on the seed layer 208 and is supported directly by the seed layer and the pillars 134, 136. In one embodiment, the gas-sensitive layer 212 is formed with a semi-conductor material including holes, and the semiconductor material is configured to undergo a reduction in a density of the holes in the presence of a target gas, thereby increasing an electrical resistance of the gas-sensitive layer 212. The gas-sensitive layer 212 includes two contact portions 250 and a serpentine portion 254 configured to extend from the sensor pillar 134 to the sensor pillar 136. The contact portions 250 are formed on the conductive layer 120c and are configured to electrically connect the sensor layer 212 to the sensor pillars 134, 136, such that electrical energy is configured to flow from the sensor pillars 134, 136 through the serpentine portion 254. The seed layer 208 is configured to electrically isolate the sensor layer 212 from the heater layer 204. Accordingly, electrically energy is prevented from flowing to the sensor layer 212 from the heater pillars 138, 140. The shape of the sensor layer 212 corresponds to the shape of the seed layer 208; accordingly, the serpentine portion 254 defines a substantially U-shaped trench in cross section that may provide further mechanical stability to the sensor portion 122. In one embodiment, the sensor layer 212 is formed from nickel oxide (NiO), which as described herein is nanostructured to be sensitive to carbon monoxide. In another embodiment, the sensor layer 212 is formed from cobalt oxide ($Co_3O_4$), which as described herein is nanostructured to be sensitive to alcohol, such as ethanol carried in the breath of an individual (i.e. breath alcohol concentration). In other embodiments, the sensor layer 212 is formed from any suitable material that is sensitive to a target gas or gasses and that is configured to be deposited into a thin film, for example using ALD. Besides being sensitive to the target gas, the sensor layer 212 may also be configured as heater in embodiments of the sensor device 100 that do not include a heater layer 204. The conductive paths 166 are first and second electrical contacts operably connected to the gas-sensitive layer 212, such that the electrical resistance, including an increase therein, can be detected by a corresponding readout circuit.

Figure 6:
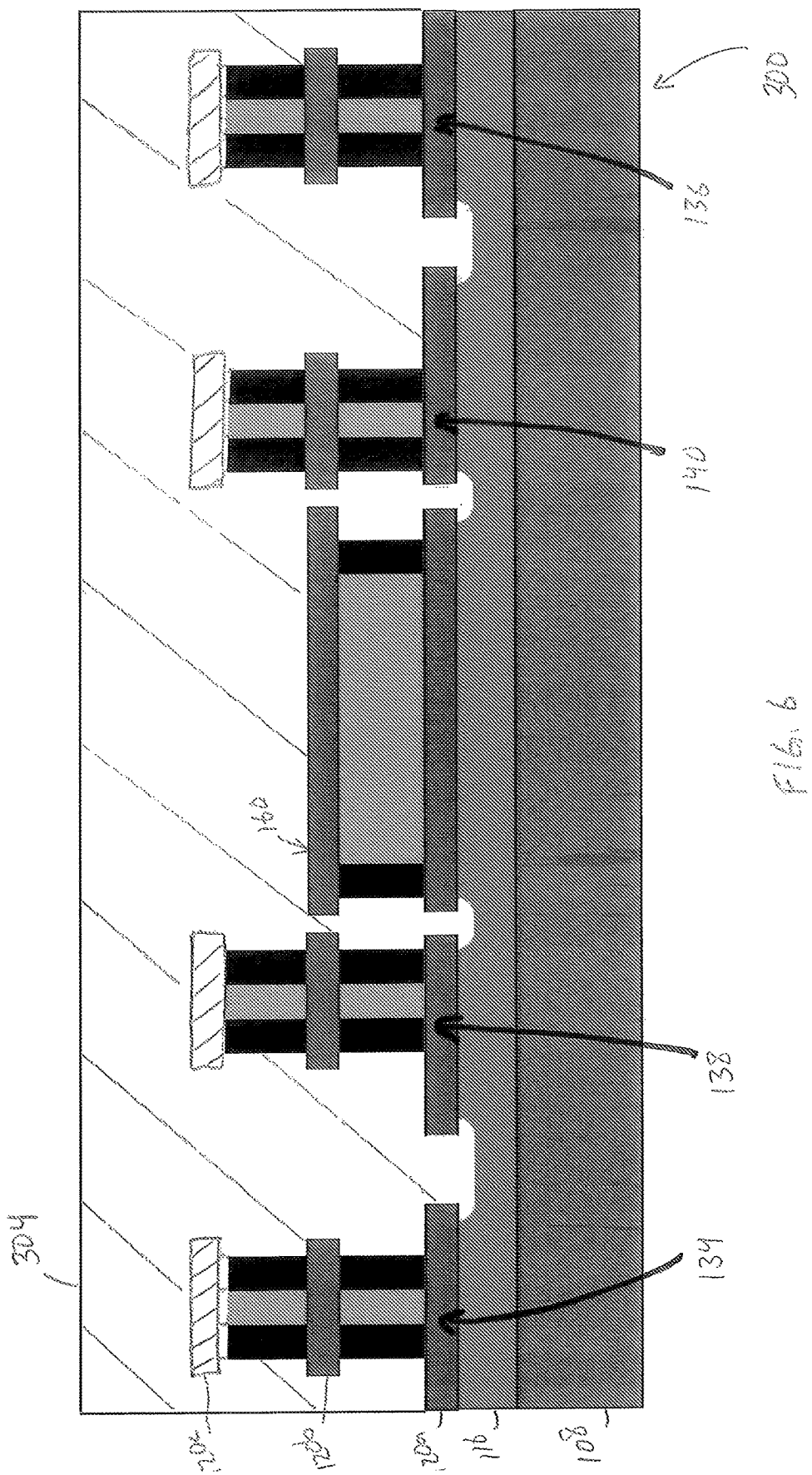
FIG. 6 is a cross sectional view taken along a line similar to the line V-V of FIG. 4, showing a sacrificial poly-silicon layer formed on a structural base of the sensor device.

With reference to FIG. 6, the sensor device 100 is fabricated/manufactured according to the following process. First, a structural base 300 is provided that includes the substrate 108, the insulator layer 116, and the conductive layers 120a, 120b, 120c, which have been patterned to define the pillars 134, 136, 138, 140 and the table 160. Then a sacrificial layer 304 is deposited over the structural base 300.

Figure 7:
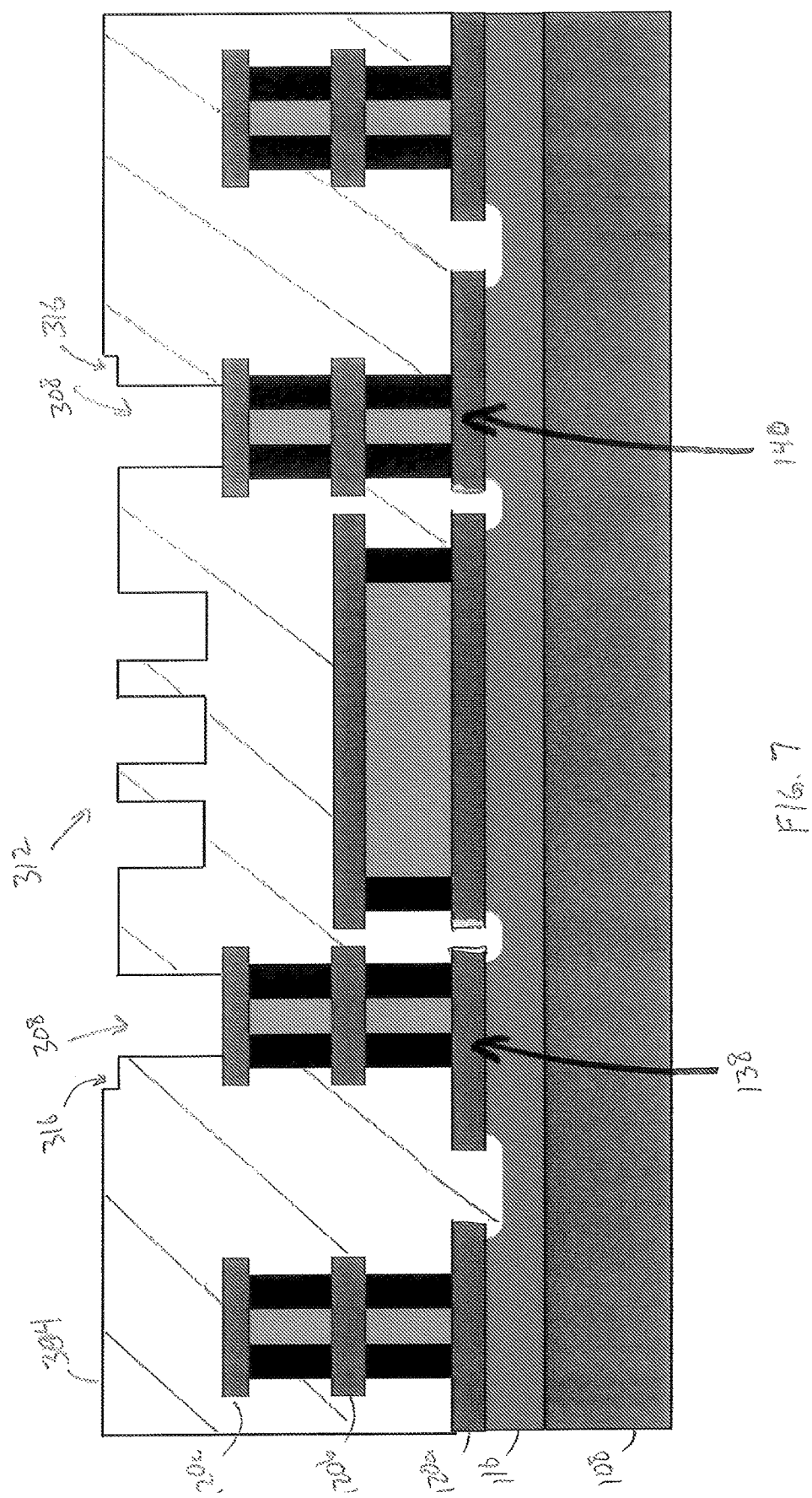
FIG. 7 is a cross sectional view taken along a line similar to the line V-V of FIG. 4, showing a trench formed in the sacrificial layer.
Figure 6:
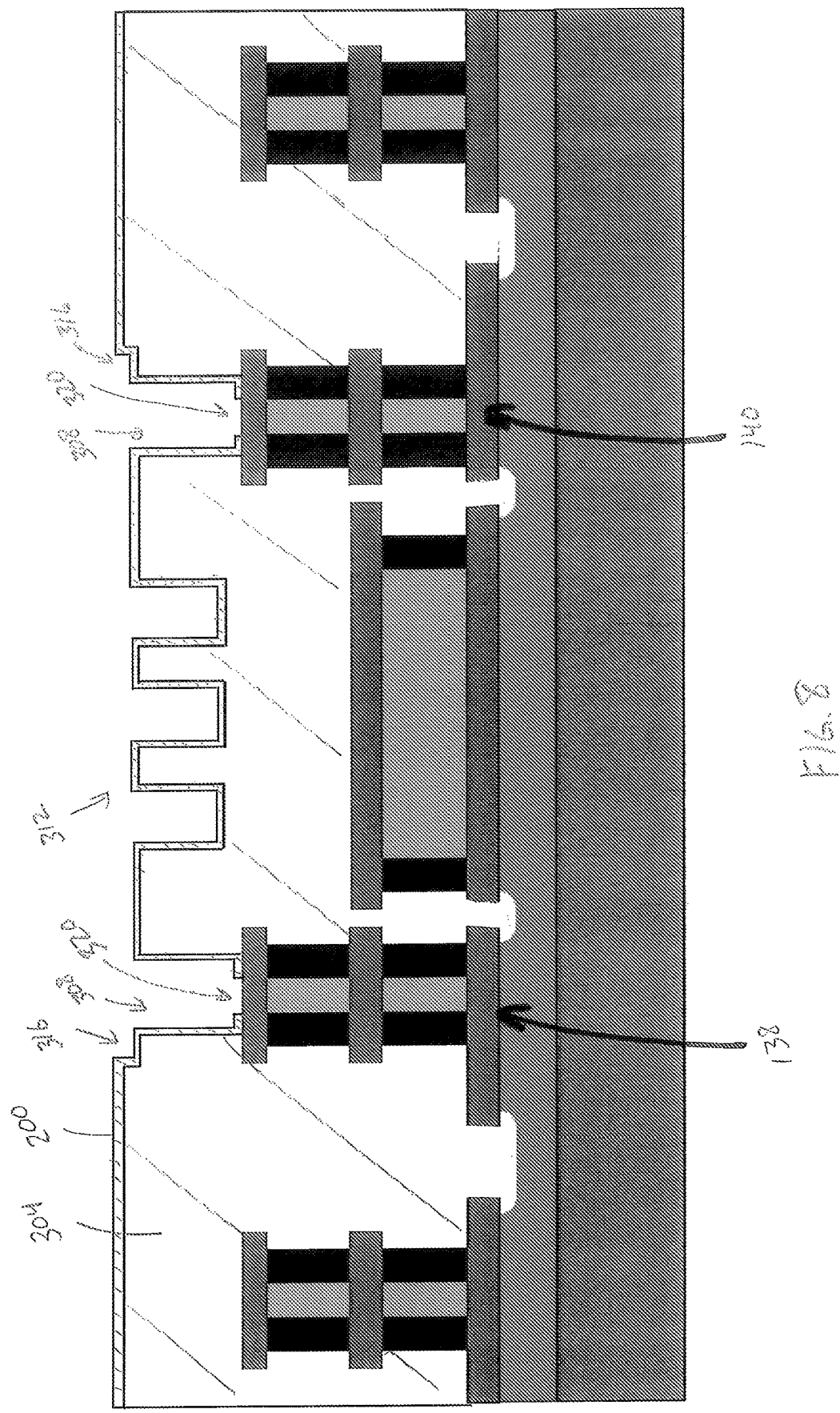

Next, as shown in FIG. 7, the sacrificial layer is patterned, with trenching for example, to define two heater trenches 308, a serpentine trench 312 (similar in shape to the serpentine structure of FIG. 4), and two notches 316. The heater trenches 308 are configured to extend from the top of the sacrificial layer 304 to the conductive layer 120*c* of the heater pillars. The serpentine trench 312 extends from the left heater trench 308 to the right heater trench 308. The notches 316 are configured to define left and right stopping points for the insulator layer 200 and the heater layer 204.

Then, as shown in FIG. 8, the insulator layer 200 is formed on the sacrificial layer 304. In one embodiment, ALD is used to form the insulator layer 200; however, any suitable chemical or physical deposition process may be used. Then, the insulator layer 200 is patterned to define two heater openings 320 that extend through the insulator layer to the conductive layer 120*c*.

Atomic layer deposition is used to deposit materials by exposing a substrate to several different precursors sequentially. A typical deposition cycle begins by exposing a substrate to a precursor "A" which reacts with the substrate surface until saturation. This is referred to as a "self-terminating reaction." Next, the substrate is exposed to a precursor "B" which reacts with the surface until saturation. The second self-terminating reaction reactivates the surface. Reactivation allows the precursor "A" to react with the surface again. Typically, the precursors used in ALD include an organometallic precursor and an oxidizing agent such as water vapor or ozone.

The deposition cycle results, ideally, in one atomic layer being formed on the substrate. Thereafter, another layer may be formed by repeating the process. Accordingly, the final thickness of the layer is controlled by the number of cycles to which the substrate is exposed. Moreover, deposition using an ALD process is substantially unaffected by the orientation of the particular surface upon which material is to be deposited. Accordingly, an extremely uniform thickness of material may be realized both on the upper and lower horizontal surfaces as well as on the vertical surfaces.

Figure 9:
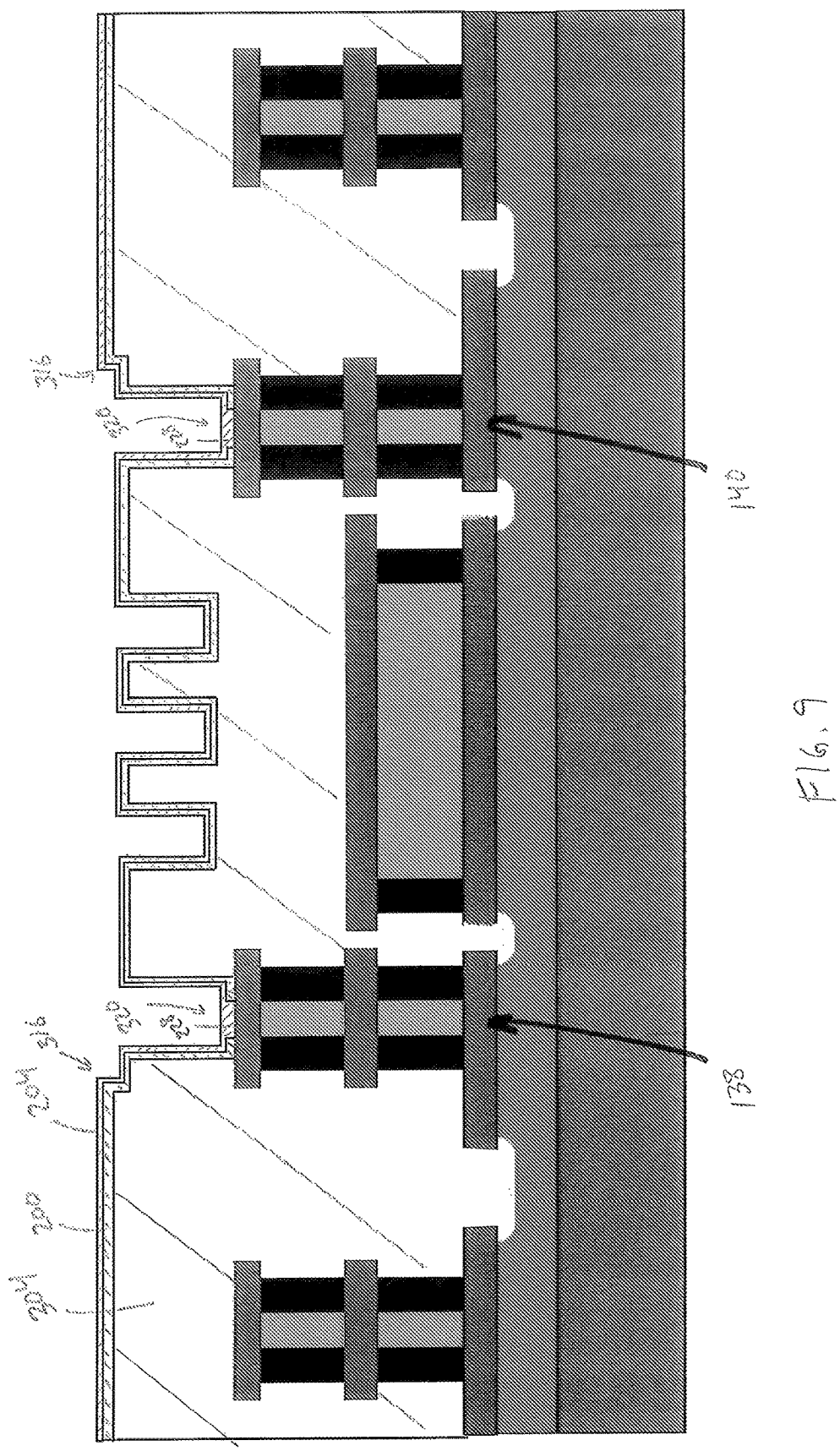
FIG. 9 is a cross sectional view taken along a line similar to the line V-V of FIG. 4, showing a heater layer formed on the insulator layer.

Thereafter, as shown in FIG. 9, the heater layer 204 is formed on the insulator layer 200. In one embodiment, ALD is used to form the heater layer 204; however, any suitable chemical or physical deposition process may be used. The material of the heater layer 204 is deposited into the heater openings 320 to form the contact portions 228, which are electrically connected to the conductive layer 120*c*.

Figure 10:
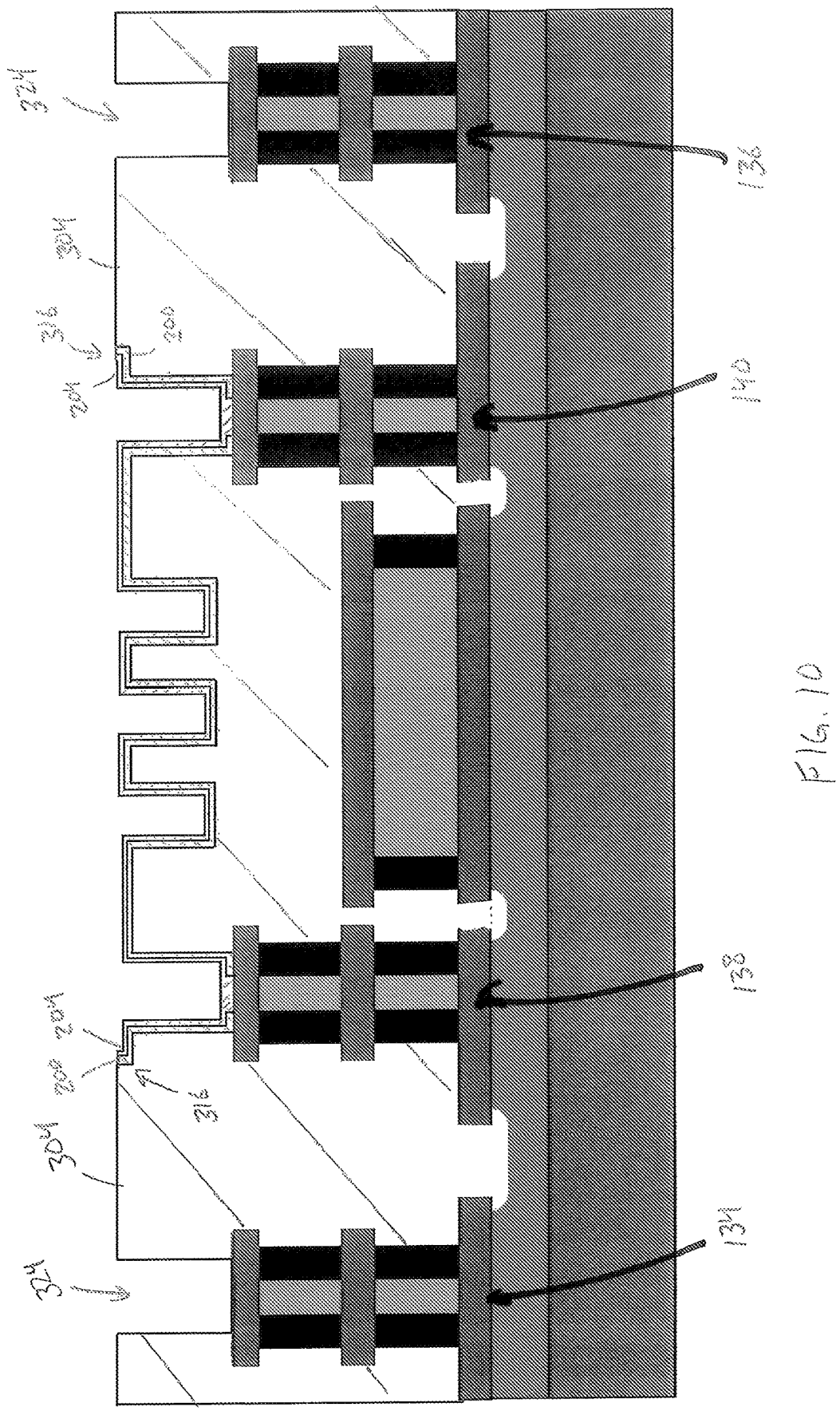
FIG. 10 is a cross sectional view taken along a line similar to the line V-V of FIG. 4, showing the insulator layer and the heater layer after patterning thereof.

Next, in FIG. 10, the sacrificial layer 304 is planarized, which includes removing portions of the insulator layer 200 and the heater layer 204 from the uppermost surface of the sacrificial layer 300 so that the uppermost surface of the sacrificial layer is exposed. After planarization, the insulator layer 200 and the heater layer only extend between the notches 316. Any suitable process may be used to planarize the insulator layer 200 and the heater layer 204 including chemical mechanical planarization (CMP).

As also shown in FIG. 10, the sacrificial layer 304 is patterned, with trenching for example, to define two sensor trenches 324. The sensor trenches 324 are configured to extend from the top of the sacrificial layer 304 to the conductive layer 120*c* of the sensor pillars 134, 136.

Figure 11:
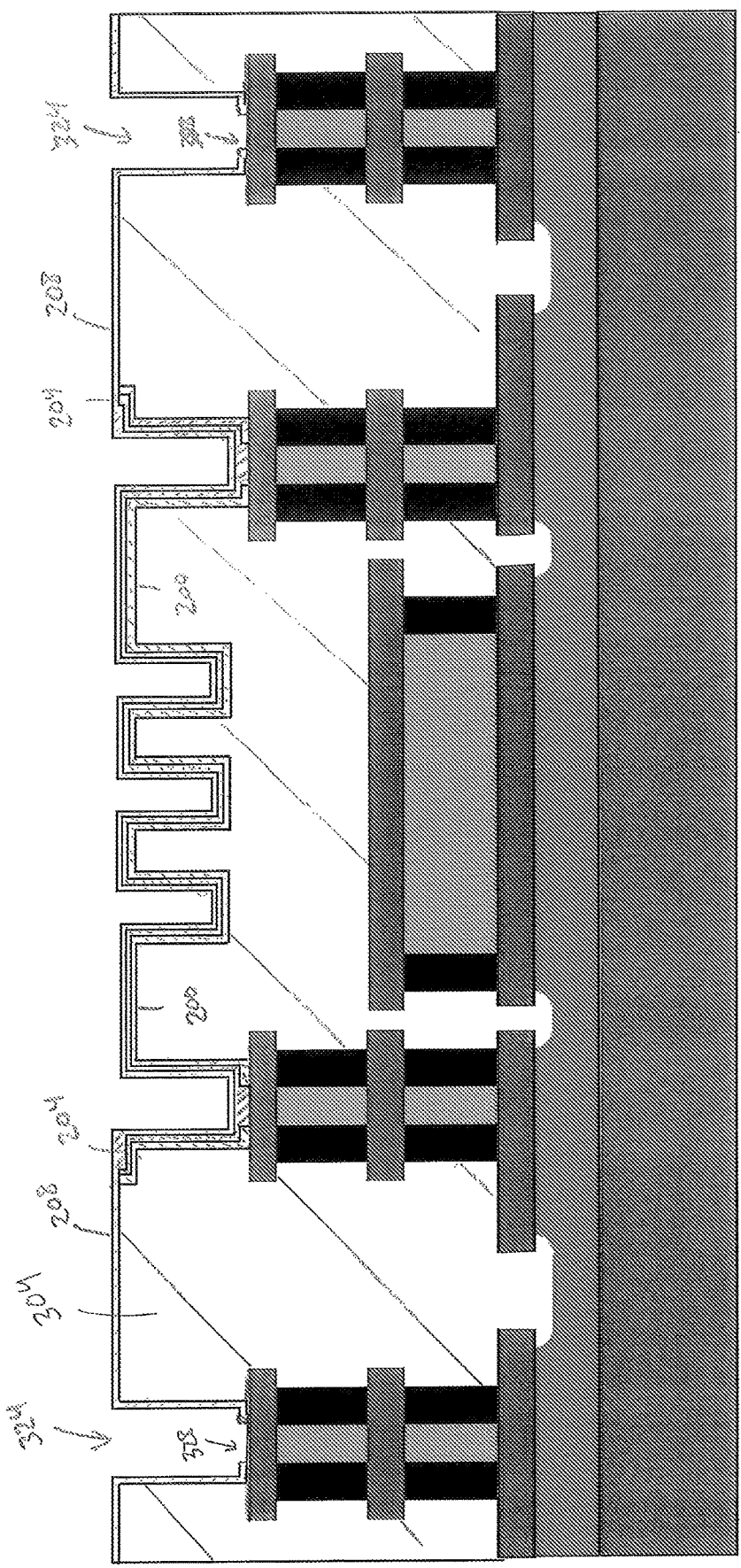
FIG. 11 is a cross sectional view taken along a line similar to the line V-V of FIG. 4, showing a seed layer formed on the sacrificial layer and on the heater layer.

Then, as shown in FIG. 11, the seed layer 208 is formed on the heater layer 204. In one embodiment, ALD is used to form the seed layer 208; however, any suitable chemical or physical deposition process may be used. The material of the seed layer 208 is deposited into the sensor trenches 324. Then, the seed layer 208 is patterned to define two sensor openings 328 that extend through the seed layer to the conductive layer 120*c*.

Figure 12:
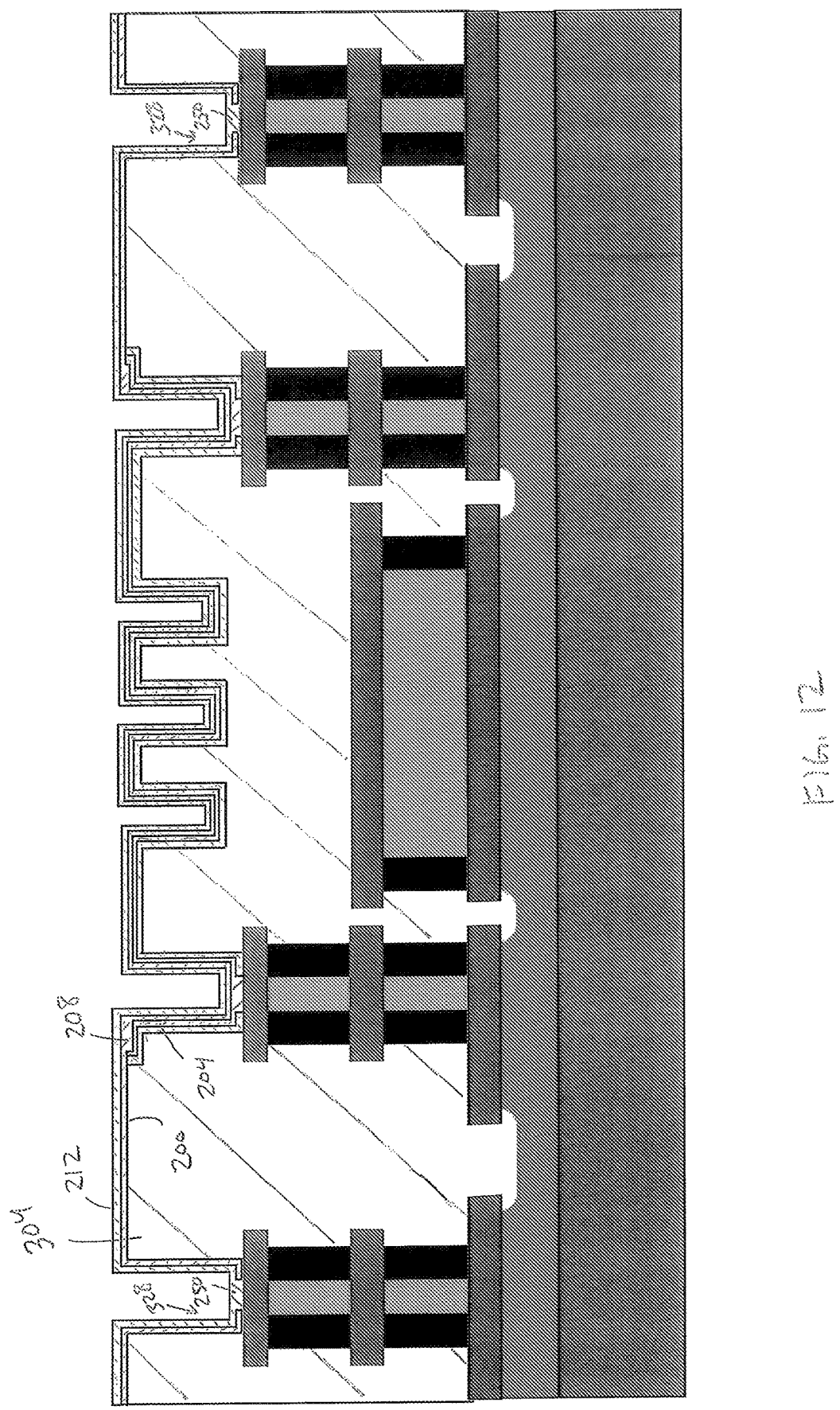
FIG. 12 is a cross sectional view taken along a line similar to the line V-V of FIG. 4, showing a sensor layer formed on the seed layer.

In FIG. 12, the sensor layer 212 is formed on the seed layer 208 as a nanostructured material. As used herein, a nanostructured material includes mostly a plurality of nanometer-sized crystallites typically arranged in the same orientation. Whereas, a bulk material (i.e. a non-nanostructured material) typically includes an amorphous molecular arrangement of mostly non-crystalline material, potentially with various sizes of crystallites interspersed amongst the non-crystalline material. Moreover, a bulk material that is generally "crystalline" is not a nanostructured material, because the crystallites of a crystalline bulk material are larger and arranged with a less uniform orientation than the crystallites of a nanostructured material.

In one embodiment, ALD is used to form the sensor layer 212 from nanostructured cobalt oxide or nickel oxide; however, any suitable chemical or physical deposition process may be used. The material of the sensor layer 212 is deposited into the sensor openings 328 to form the contact portions 250, which are electrically connected to the conductive layer 120*c*.

As described above, nickel oxide is a suitable material for forming the sensor layer 212. In an exemplary embodiment, ALD is used to deposit nanostructured nickel oxide at a deposition temperature of 160° C. to 200° C. to form the sensor layer 212. Typically, the ALD deposited nickel oxide exhibits a high growth rate of approximately five nm/min and has excellent step coverage up to an aspect ratio of approximately 50:1. Therefore, forming the sensing layer 212 using ALD is much faster and simpler than forming thick films of nickel oxide. In particular, to form a thick film of nickel oxide, nickel nitrate hexahydrate is dissolved into 20 ml of equal amounts isopropyl alcohol (IPA) and polyethylene glycol to make a 0.1M solution. Then the solution is stirred for one hour (at 25° C.) until the solution becomes transparent. Next, an alkali free glass substrate is coated with the solution and is heated to 350° C. to evaporate the solvent and to leave behind a layer of nanostructure NiO particles. The process is repeated until a desired thickness is achieved. Thus, ALD offers the fabricator the advantage of being able to form the sensor layer 212 quickly and easily.

After forming the sensor layer 212, the suspended sensor portion 122 may be patterned to finalize its serpentine shape. Then, the sacrificial layer 304 is released/removed using xenon difluoride ($XeF_2$) or any other suitable release agent. Removal of the sacrificial layer 304 suspends the suspended sensor portion 122 above the conducting layers 120*a*, 120*b*, 120*c* as shown in FIG. 5.

Figure 13:
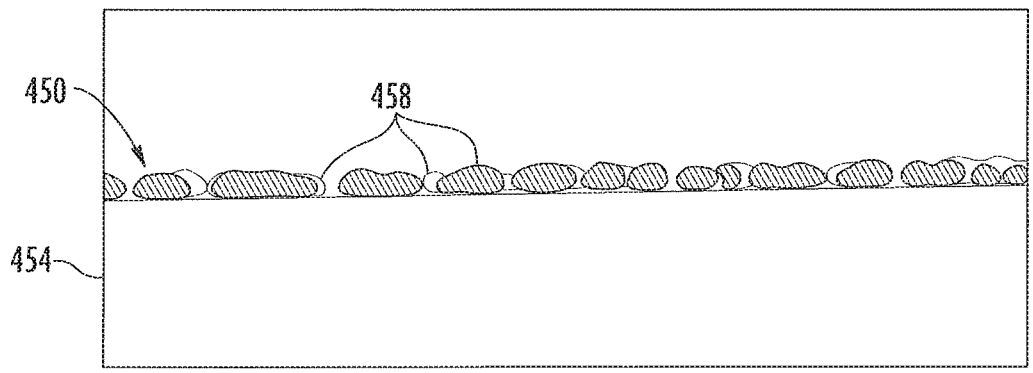
FIG. 13 is a depiction of a transmission electron microscope view of a platinum layer formed using a process that is suitable for forming the sensor layer of the sensor device described herein.
Figure 14:
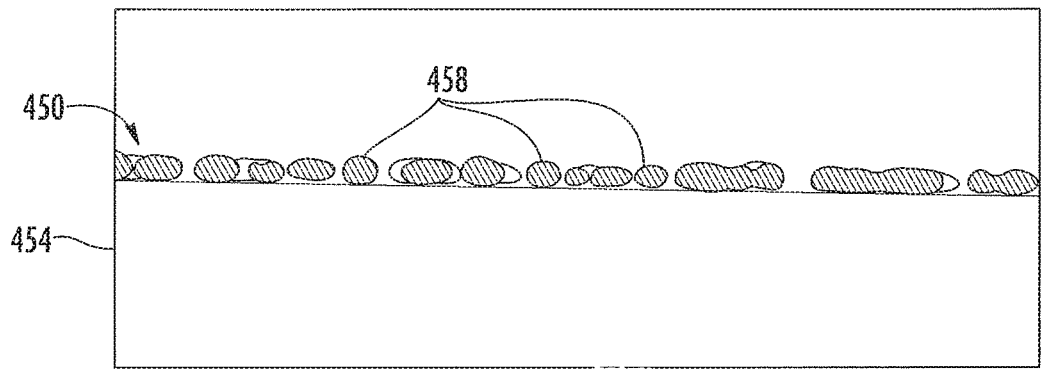
FIG. 14 is another depiction of a transmission electron microscope view of a platinum layer formed using the process that is suitable for forming the sensor layer of the sensor device described herein.

In forming the sensor device 100, the materials of the seed layer 208 and the sensor layer 212 are selected to achieve a desired porosity of the sensor layer. FIGS. 13 and 14 show two schematics of microscope views of an exemplary sensor layer 450 and a seed layer 454 that were formed from a non-suitable pair of materials. The seed layer 454 is formed from silicon dioxide and the deposited material of the sensor layer 450 is platinum. Accordingly, silicon dioxide and platinum form an exemplary pair of non-suitable materials, because ALD deposition of the material of the sensor layer results in the formation of nucleated grains 458 (granular structure) instead of a continuous solid (non-porous) surface. In FIG. 13, approximately one hundred fifty cycles of ALD were performed at approximately 270° C. In FIG. 14, approximately one hundred twenty five cycles of ALD were performed at approximately 270° C. The reduction in cycles results in smaller grains 458 and more space between each grain 458, thereby increasing the porosity of the sensor layer.

Accordingly, in one embodiment, the material of the seed layer 208 is selected to react with the material of the sensor layer 212 to achieve a desired porosity of the sensor layer 212 and/or a desired grain size of the sensing layer. In such an embodiment, the material of the seed layer 208 is selected to be a "non-suitable" material. The term "non-suitable material" is defined herein as a material that when used as a seed layer for a particular sensor layer material, causes spaced-apart nucleation of grains of the sensor layer 212 during depositing of the sensor layer 212. In another embodiment, the material of the seed layer 208 is selected as a "suitable material" that results in a substantially contiguous layer of the sensing material during depositing/formation of the sensor layer 212.

Additionally, the seed layer 208 may be structured with trenching (or any other desired process) to further encourage spaced-apart nucleation of the sensor layer 212. In one specific embodiment, the "structuring" includes patterning the seed layer 208 and/or chemically activating certain spaced-apart nucleation sites in order to encourage spaced-apart nucleation of grains of the sensor layer 212. In yet another embodiment, the "structuring" includes ion-milling the seed layer 208 with passive gasses, such as argon, to make the seed layer more dense or less dense at spaced-apart nucleation sites, thereby resulting in selective encouragement of spaced-apart nucleation of the sensor layer 212. In general, the seed layer 208 is formed and/or structured from any material(s) and by any process(es) that encourages a desired level of spaced-apart nucleation of the sensor layer 212 on the seed layer.

According to another exemplary embodiment a method of fabricating the thin film gas sensor device 100 includes providing the substrate 108 and supporting the pillars 134, 136 with the substrate 108. Then the nanostructured thin film layer 212 is formed using a semi-conductor material including holes. The semiconductor material is configured to undergo a reduction in a density of the holes in the presence of the target gas thereby increasing an electrical resistance of the nanostructured thin film layer 212. The method further comprises operably connecting the first and the second electrical contacts, such as the conductive paths 166 for example, to the nanostructured thin film layer 212, such that the increase in electrical resistance can be detected. The nanostructured thin film layer 212 may be formed from nickel oxide (NiO) or cobalt oxide ($Co_3O_4$) using atomic layer deposition. Also, the sacrificial layer 304 may be formed above the substrate 108, and the seed layer 208 may be formed from a first material above the substrate 108. The nanostructured thin film layer 212 is formed from a second material on the seed layer 208. The sacrificial layer 304 is removed to suspend a suspended portion of the seed layer 208 and the nanostructured thin film layer 212 above the substrate 108.

In operation, the sensor device 100 is configured to sense the presence of a target gas or target gasses in a space in which the sensor device is positioned. In one example, the sensor layer 212 is formed from nickel oxide, and the target gas is carbon monoxide. In another example, the sensor layer 212 is formed from nanostructured cobalt oxide, and the target gas is alcohol. Due at least to the extremely small form factor of the sensor device 100, as compared to prior art thick film MOS gas sensors, the sensor device 100 is usable to detect gasses in a variety of applications such as automobile exhaust systems, home appliances, laptops, handheld or portable computers, mobile telephones, smart phones, wireless devices, tablets, personal data assistants (PDAs), portable music players, film cameras, digital cameras, GPS receivers and other satellite navigation systems, electronic reading displays, projectors, cockpit controls, game consoles, earpieces, headsets, hearing aids, wearable display devices, security systems, breath analysis devices (breathalyzer), and other applications as desired by those ordinary skill in the art.

Use of the sensor device 100 includes applying an electrical current directly to the heater layer 204 through the heater pillars 138, 140 with an electrical energy source (not shown). In response to the electrical current, the heater layer 204, which operates as a Joule heater, quickly heats the sensor layer 212 to a desired sensing temperature (i.e. a predetermined operating temperature) that is based at least on a magnitude of the electrical energy source and an electrical resistance of the heater layer 204. A very low heating power is used to heat the sensor layer 212 (approximately 3.5 mW when heated to 350° C.) to the desired sensing temperature due to the layer 212 being suspended and due to the layer 212 being very thin. Also, the suspended structure enables the sensor layer 212 to be heated to a first temperature while enabling the substrate 108, the insulator layer 116, and the conductive layers 120a, 120b, 120c to remain at a second temperature that is different (i.e. lower) than the first temperature. Since the sensor layer 212 is spaced apart from the insulator layer 116 and the substrate 108, substantially no heat energy is used to heat the insulator layer and the substrate during heating of the sensor layer 212. Although some of the heat energy developed by the heater layer 204 is used to heat the air surrounding the layer suspended sensor portion 122, substantially all of the heat energy is used to heat the sensor layer 212. Furthermore, the serpentine shape of the suspended sensor portion 122 results in the sensor layer 212 efficiently converting electrical energy into heat energy.

The sensor layer 212 is heated to the sensing temperature within a heating time period, which is referred to herein as a thermal time constant. The thermal time constant begins when electrical energy is applied to the heater layer 204 and ends when the sensor layer 212 is heated to the sensing temperature. Due at least to the thinness and the structure of the suspended sensor portion 122, the sensor device 100 has an extremely low thermal time constant on the order of 3 milliseconds. Accordingly, the low thermal time constant allows for duty cycling for low power operation (35 µW at 1% duty cycle). Furthermore, the sensor layer 212 is configured for fast temperature changes, ultimately resulting in fast detection of the target gas.

The sensing temperature of the sensor layer 212 is based on properties of the target gas and the environment/space in which the assembly 100 is positioned. Exemplary sensing temperatures range from 150° C. to 500° C.; however, the sensor device 100 is configurable to operate at any desired sensing temperature. In one embodiment, a sensing temperature of 330° C. (i.e. predetermined operating temperature) was determined to be a suitable sensing temperature for a sensing layer 212 formed from nanostructured nickel oxide. In another embodiment, a sensing temperature of 350° C. (i.e. predetermined operating temperature) was determined to be a suitable sensing temperature for sensing alcohol with a sensing layer 212 formed from nanostructured cobalt oxide. In yet another embodiment, a sensing temperature of 400° C. (i.e. predetermined operating temperature) was determined to be a suitable sensing temperature for sensing alcohol with a sensing layer 212 formed from nanostructured cobalt oxide.

After being heated to an operating temperature, the sensor device 100 is exposed to an environment in which the target gas (carbon monoxide or alcohol for example) may or may not be present. Thereafter, an external read out circuit uses the electrical resistance of the sensor layer 212 as measured from the sensor pillar 134 to the sensor pillar 136 to determine if the target gas is present in the environment. Specifically, a voltage drop across a reference resistor (not shown) connected in series with the sensor layer 212 is detected/monitored by the external circuit. In response to the target gas, the electrical resistance of the sensor layer 212 changes, thereby impacting the voltage dropped across the reference resistor. Thus, the magnitude of the voltage dropped across the reference resistor is used to determine the concentration, presence, and/or absence of the target gas in the environment. Accordingly, the read out circuit for the sensor device 100 is much simpler than the read out circuit that is configured to operate an optical based carbon monoxide detector.

In addition to preparing the sensor layer 212 for detecting and/or exposure to the target gas, the heater layer 204 may also be heated to "reset" the gas sensor 100 through desorption. During desorption molecules are evacuated from the sensor layer 212 in order to prepare the sensor device 100 for sensing additional quantities of the target gas.

As described above, in one embodiment, ALD is used to form the sensing layer 212 from nanostructured nickel oxide. The nickel oxide is nanostructured in order for the material to achieve the desired sensing effects, because the sensitivity of nickel oxide to carbon monoxide is a surface phenomenon and nanostructuring greatly increases the surface area of the material as compared to bulk nickel oxide, which typically exhibits substantially no sensitivity to gases due to a very low surface area to volume ratio. Furthermore, bulk nickel oxide is typically an insulator, however ALD deposited nanostructured nickel oxide includes nickel vacancies or interstitial oxygen atoms, thereby resulting in a material with semiconductor like electrical conductivity. Typically, nanostructured nickel oxide functions as a p-type semiconductor.

The sensing effect of the nickel oxide sensing layer 212 occurs in response to carbon monoxide combining with $O^-$ (anion) radicals on the surface of the nickel oxide to form carbon dioxide, resulting in a decrease in $O^-$ density in the nickel oxide. The reduction in anion density leads to a reduction in the density of holes in the semiconductor, thereby increasing the electrical resistance of the nickel oxide. The sensor device 100 uses this effect to produce a carbon monoxide sensor that exhibits a simple change in resistance instead of the traditional and more complex optical carbon monoxide sensor.

Figure 16:
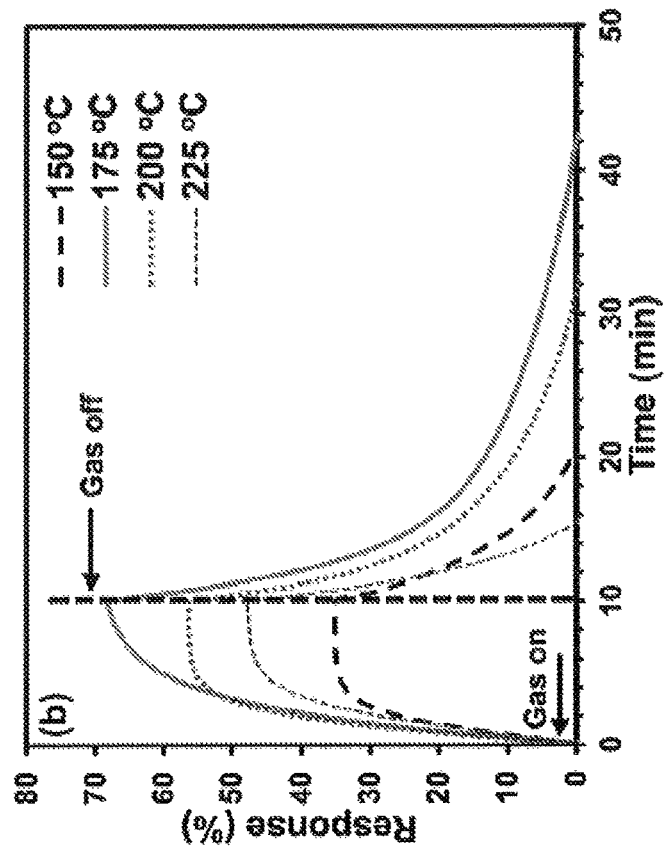
FIG. 16 is a graph showing a response time and a recovery time for four different operating temperatures of a thin film structure suitable for forming the sensor layer of the sensor device described herein.
Figure 15:
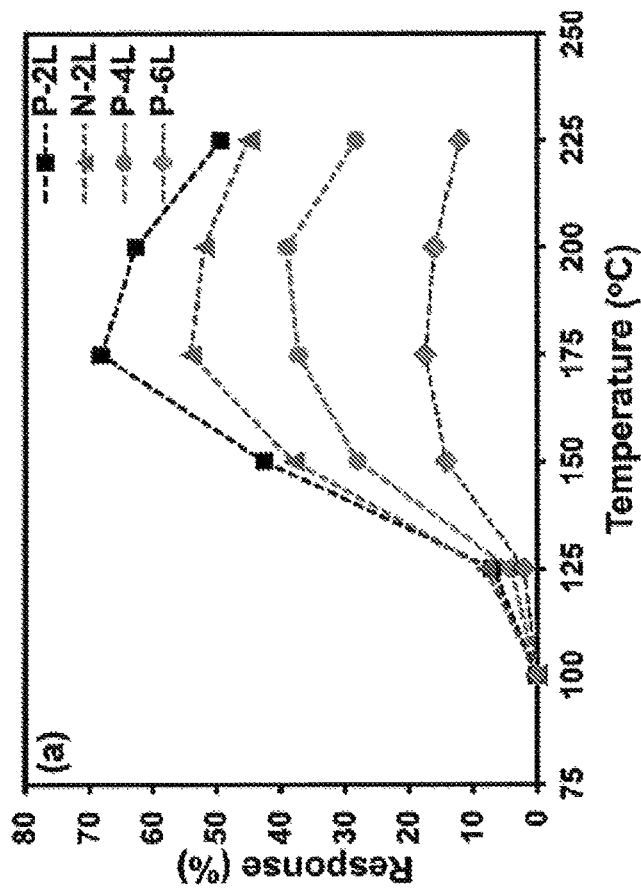
FIG. 15 is a graph of response percentage versus temperature for four different thin film structures suitable for forming the sensor layer of the sensor device described herein.

In addition to being sensitive to carbon monoxide, the nanostructured nickel oxide sensor layer 212 is also sensitive to other gases including hydrogen ($H_2$) and hydrogen based gasses. The sensitivity of nickel oxide to hydrogen is also a surface phenomenon. In particular, hydrogen reacts with oxygen radicals on the surface of nickel oxide to form water ($H_2O$) and to release electrons to the nickel oxide (that functions as a p-type semiconductor), which combine with electron holes in the material. The resulting reduction in the available electron holes increases the electrical resistance of the nickel oxide. As expected, the size and porosity of the grains of nickel oxide determine, at least in part, the sensitivity of the sensor layer 212 to hydrogen. As shown in the graphs of FIGS. 15 and 16, the response of the sensor layer 212 to 3000 ppm hydrogen in an environment of air is plotted as a response percentage according to the following equation:

$$\text{Response } \% = 100\left[\frac{R_{Gas} - R_{Air}}{R_{Air}}\right]$$

In the above equation, the resistance of the sensor layer 212 in air $R_{Air}$ is compared to the resistance of the sensor layer 212 in the presence of hydrogen $R_{Gas}$. As shown in FIG. 15, the response percentage versus temperature is plotted for four different thin film structures (P-2L, N-2L, P-4L, and P-6L). The P-2L structure includes two layers of nickel oxide and defines a thickness of 16 mm and a surface area of 51.69 m$^2$/g. The N-2L structure includes two layers of nickel oxide and defines a thickness of 19 mm and a surface area of 35.55 m$^2$/g. The P-4L structure includes four layers of nickel oxide and defines a thickness of 29 mm and a surface area of 21.36 m$^2$/g. The P-6L structure includes six layers of nickel oxide and defines a thickness of 46 mm and a surface area of 18.58 m$^2$/g. As shown as FIG. 15, the response percentage of each thin film structure peaks at an operating temperature of 175° C. In FIG. 16 the response percentage of the P-2L thin film structure is plotted verses time to illustrate the response time and the recovery time for four operating temperatures including 150° C., 175° C., 200° C., and 225° C., and the response percentage peaks again at 175° C.

According to yet another exemplary embodiment, a method of using the thin film gas sensor device 100 includes obtaining a first electrical resistance reading across the nanostructured thin film layer 212. The nanostructured thin film layer 212 includes a semi-conductor material including holes, and the semiconductor material is configured to undergo a reduction in a density of the holes in the presence of the target gas thereby increasing an electrical resistance of the nanostructured thin film layer 212. The method further comprises exposing the nanostructured thin film layer 212 to a gaseous environment after obtaining the first reading. Then a second electrical resistance reading is obtained across the nanostructured thin film layer 212 after exposing the nanostructured thin film layer 212 to the gaseous environment. Thereafter, the first obtained reading and the second obtained reading are compared. The presence, absence, or concentration of the target gas is determined based on the comparison of the first obtained reading and the second obtained reading.

In one embodiment, the first and second electrical resistance readings are obtained with the nanostructured thin film layer 212 at a first temperature, and then the nanostructured thin film layer 212 is heated to a second temperature prior to exposing the nanostructured thin film layer to the gaseous environment. The second temperature is different from the first temperature. Thereafter, a third electrical resistance reading is obtained across the nanostructured thin film layer 212 with the nanostructured thin film layer 212 at the second temperature prior to exposing the nanostructured thin film layer 212 to the gaseous environment. Then, a fourth electrical resistance reading is obtained across the nanostructured thin film layer 212 with the nanostructured thin film layer 212 at the second temperature after exposing the nanostructured thin film layer 212 to the gaseous environment. Next, the third obtained reading and the fourth obtained reading are compared, and it is determined if the target gas is present based upon the comparison of the first obtained reading, the second obtained reading, the third obtained reading, and the fourth obtained reading.

Figure 17:
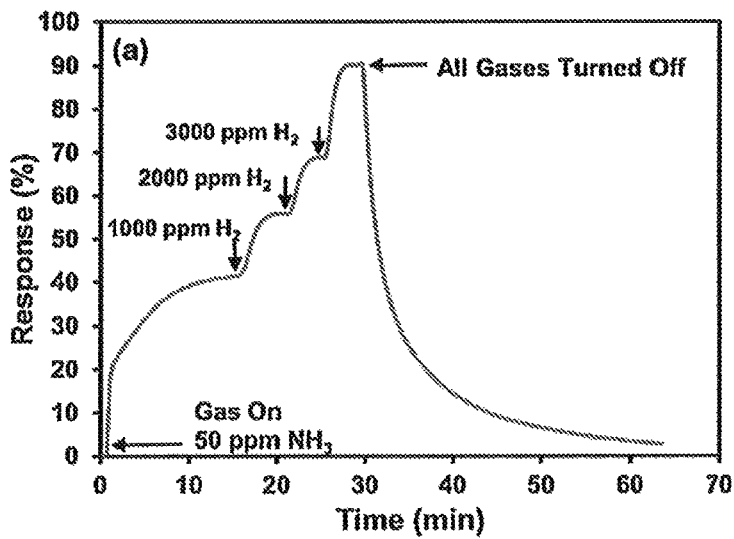
FIG. 17 is a graph of response percentage versus time of a nickel oxide sensor layer exposed to hydrogen in an environment of 50 ppm ammonia ($NH_3$)
Figure 18:
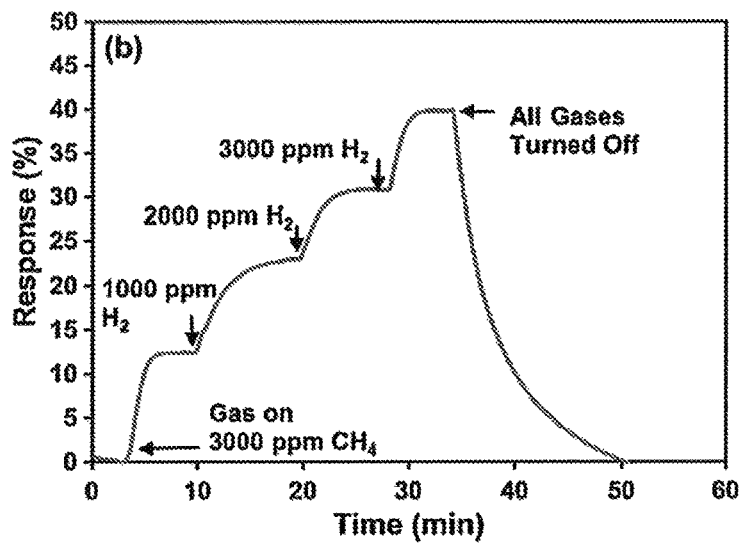
FIG. 18 is a graph of response percentage versus time of a nickel oxide sensor layer exposed to hydrogen in an environment of 3000 ppm methane ($CH_4$)
Figure 19:
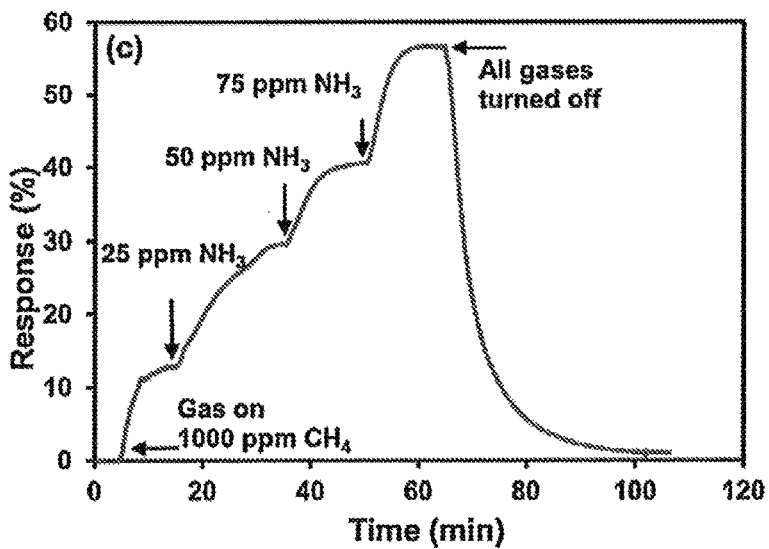
FIG. 19 is a graph of response percentage versus time of a nickel oxide sensor layer exposed to ammonia in an environment of 1000 ppm methane.
Figure 20:
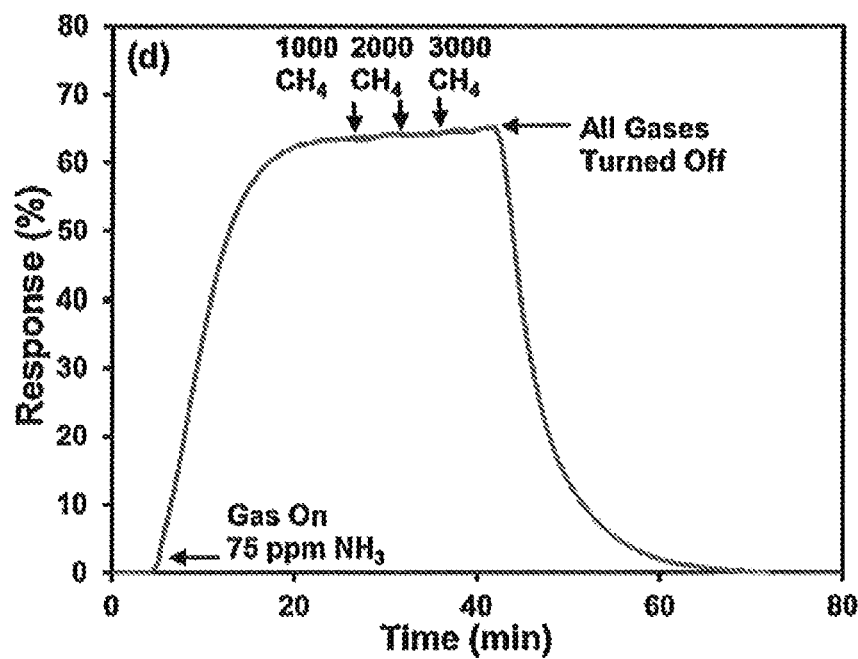
FIG. 20 is a graph of response percentage versus time of a nickel oxide sensor layer exposed to methane in an environment of 75 ppm ammonia.
Figure 21:
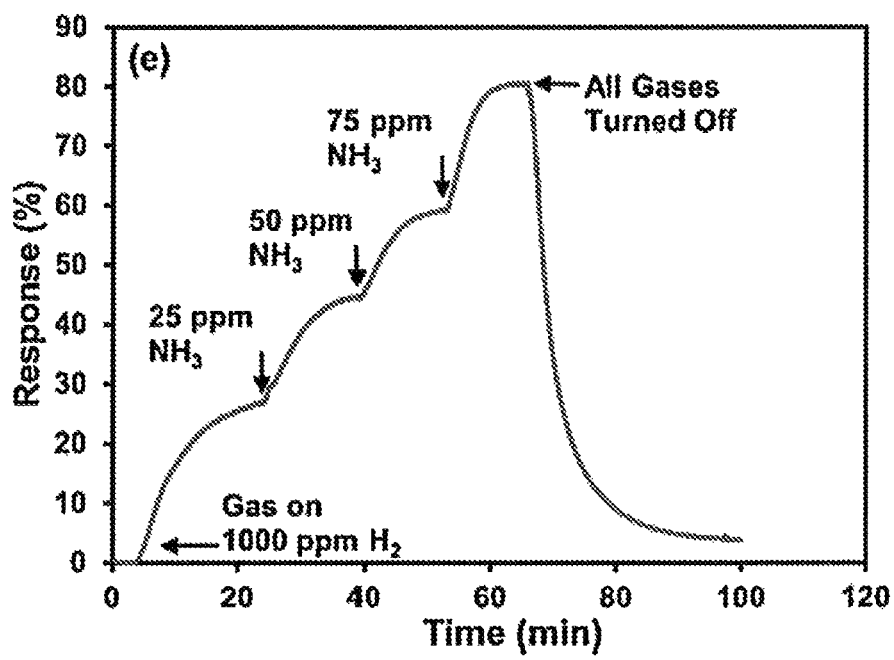
FIG. 21 is a graph of response percentage versus time of a nickel oxide sensor layer exposed to methane in an environment of 1000 ppm hydrogen

FIGS. 17-21 plot the cross sensitivity responses and recovery times of a sensor layer 212 formed from nanostructured nickel oxide in presence of hydrogen and other hydrogen based gases, as may occur, for example, in the exhaust product of an internal combustion engine. As shown in FIGS. 17 and 18, the sensor layer 212 exhibits a high selectivity towards hydrogen in a hydrogen and ammonia mixture (FIG. 17) and a hydrogen and methane mixture (FIG. 18). In FIG. 19 the sensor layer 212 exhibits a high selectivity towards hydrogen in a hydrogen and ammonia mixture (FIG. 17) and a hydrogen and methane mixture (FIG. 18). In FIG. 19 selectivity towards ammonia is shown in a mixture of ammonia and methane. In FIG. 20 a low selectivity toward methane is shown in a mixture of methane and ammonia. In FIG. 21 a selectivity towards ammonia is shown in a mixture of ammonia and hydrogen.

The above graphs (FIGS. 17-21) demonstrate that a sensor layer 212 formed from nanostructured nickel oxide exhibits a strong cross sensitivity to hydrogen-based gases. Accordingly, the external read out circuit is configurable with smart algorithms and the like to compare the variation in sensitivity, selectivity, and response percentage at different operating temperatures of the sensor device 100 in order to detect a variety of gases with a single sensor device 100.

Figure 22:
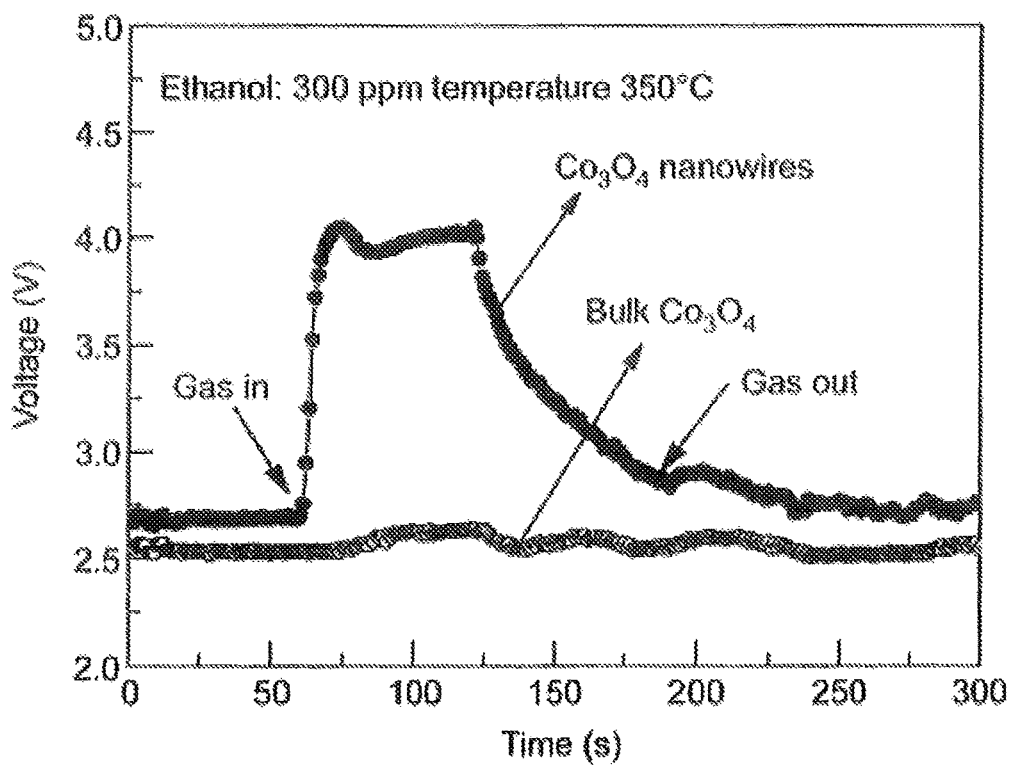
FIG. 22 is a graph illustrating a voltage drop versus time for bulk cobalt oxide and nanostructured cobalt oxide, the graph shows that bulk cobalt oxide has substantially zero voltage response to alcohol and that nanostructured cobalt oxide has significant voltage response to alcohol.

With reference to FIG. 22, in another embodiment ALD is used to form the sensing layer 212 from nanostructured cobalt oxide instead of bulk cobalt oxide. The cobalt oxide is nanostructured in order for the material to achieve the desired sensing effects, because the sensitivity of cobalt oxide to alcohol is a surface phenomenon and nanostructuring greatly increases the surface area of the material as compared to bulk cobalt oxide, which typically exhibits substantially no sensitivity to alcohol due to a very low surface area to volume ratio. This phenomenon is illustrated in FIG. 22, in which it is shown that a voltage drop across bulk cobalt oxide exhibits substantially no change in response to 300 ppm of ethanol alcohol, whereas nanostructured cobalt oxide (i.e nanowires formed with solvothermal reactions) exhibits an increased voltage drop at approximately the sixty second mark in response to the introduction of alcohol to the environment. FIG. 22 also shows that the response time of nanostructured cobalt oxide (formed with solvothermal reactions) is very fast with a delta of approximately 1.25 V in approximately 2-3 seconds.

Another reason that nanostructured cobalt oxide is used in the sensing layer 212, is that bulk cobalt oxide is typically an insulator, but nanostructured cobalt oxide functions a p-type semiconductor having an electrical resistance that is based on the concentration of alcohol in the environment to which it is exposed. In particular, the surface of nanostructured cobalt oxide contains chemisorbed oxygen that provides electron holes for conduction according to the following equation:

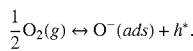

The surface of nanostructured cobalt oxide includes O$^-$ (anion) species that readily oxidize ethanol (C$_2$H$_5$OH) by removing the electron holes the cobalt oxide, thereby increasing the electrical resistance of the sensing layer 212 according to the following equation:

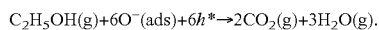

The sensor device 100 uses this effect to produce an alcohol sensor that exhibits a simple change in resistance to detect alcohol in an environment.

Figure 23:
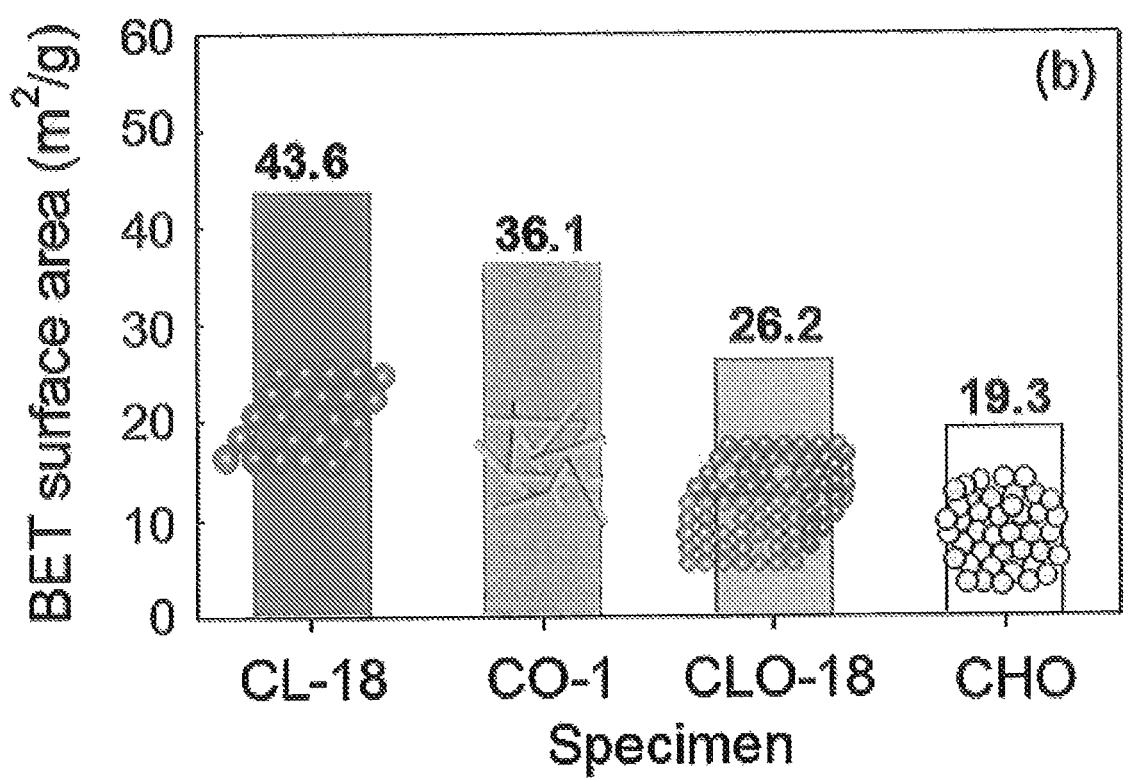
FIG. 23 is a graph of the Brunauer-Emmett-Teller Method surface areas of four nanostructures of cobalt oxide including nanosheets, nanowires, nanocubes, and agglomerated powder, the nanostructures being formed by solvothermal reaction.
Figure 24:
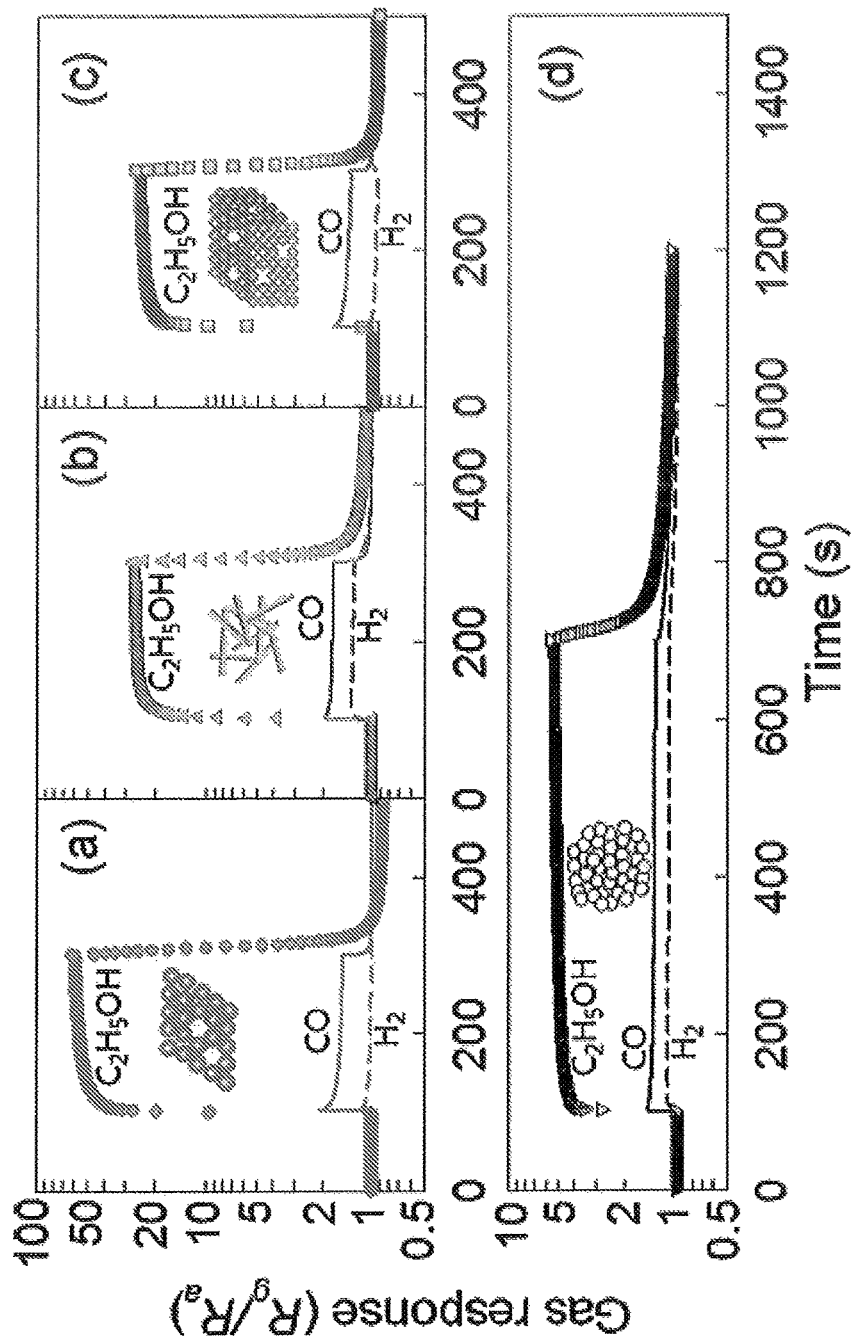
FIG. 24 includes four graphs showing the gas response of the four nanostructures of cobalt oxide of FIG. 23.

Of the various types of nanostructured cobalt oxide, cobalt oxide deposited with ALD shows the overall most suitable electrical response to alcohol, and is the type of nanostructured cobalt oxide used to form the sensor layer 212, in at least one embodiment. To confirm this assertion, as shown in FIG. 23, the Brunauer-Emmett-Teller Method surface area (BET surface area) of four different nanostructures of cobalt oxide is shown including nanosheets (Cl-18), nanowires (CO-1), nanocubes (CLO-18), and agglomerated powder (CHO) each of which is formed via solvothermal reactions. Cobalt oxide structured as a nanosheet has the highest surface area per gram of the tested structures, and therefore should have the highest response rate of the tested structures. This assertion is confirmed in FIG. 24, which shows that the gas response of nanosheet cobalt oxide has the highest response. In FIG. 24, the gas response of the materials is a "unitless" quantity measured as the quotient of measured resistance of the material in the presence of the target gas in air and the measured resistance of the material in the presence of air only.

FIGS. 23 and 24 confirm that the magnitude of the gas response is related to the surface area of the materials. As described above, ALD is usable to form a planar surface only a few atoms thick, and that has as an even higher BET surface area than nanosheet structured cobalt oxide. Therefore, a sensor layer 212 formed with ALD deposited cobalt oxide has an even greater magnitude of gas response, than the nanosheet cobalt dioxide formed with solvothermal reactions of FIG. 24.

Figure 25:
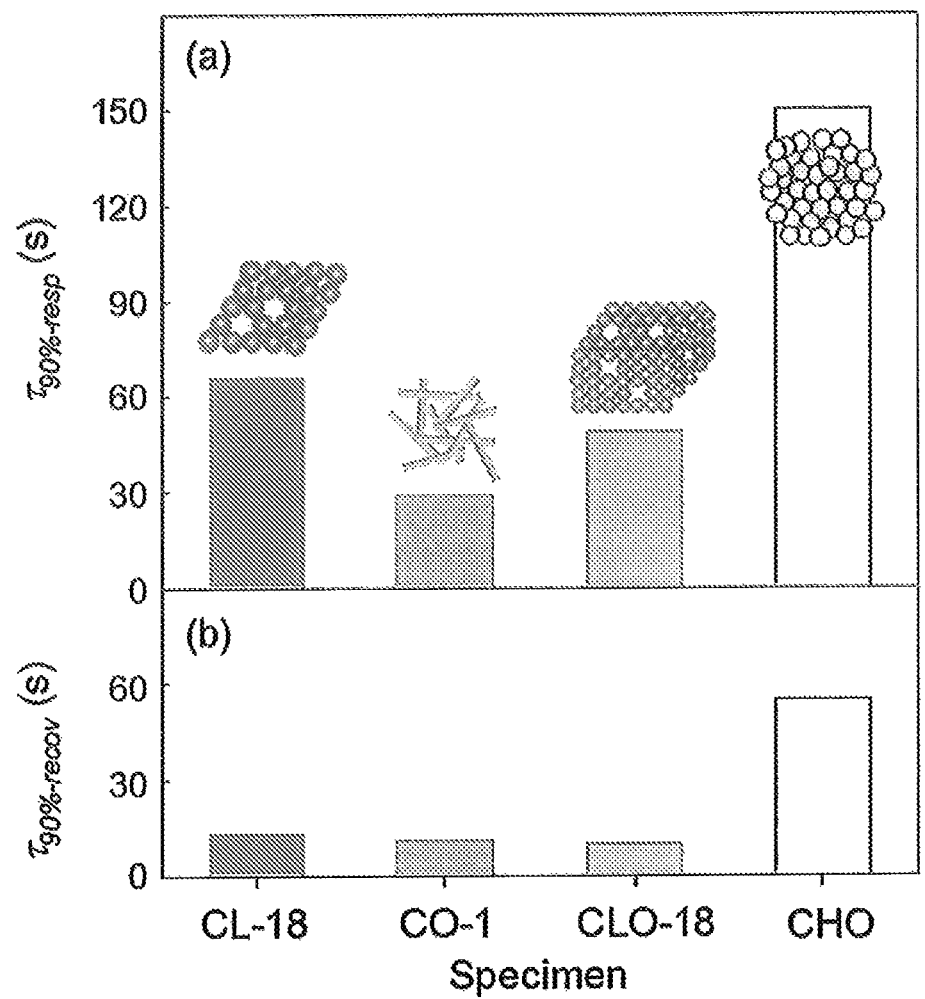
FIG. 25 includes two graphs showing the response time and the recovery time of the four nanostructures of cobalt oxide of FIG. 23.

FIG. 25 illustrates the response (graph (a)) and recovery times (graph (b)) of various types of nanostructured cobalt oxide in response to alcohol. As shown in graph (a), the 90% response time of nanosheet (CL-18) cobalt oxide is approximately sixty seconds, which is greater than nanowires (CO-1) and nanocube (CLO-18) cobalt oxide, and much less than agglomerated powder (CHO) cobalt oxide. As shown in graph (b), the 90% recovery time for each of nanosheet, nanowire, and nanocube cobalt oxide is approximately fifteen seconds, much less than the sixty second recovery time of agglomerated powder cobalt oxide.

Figure 26:
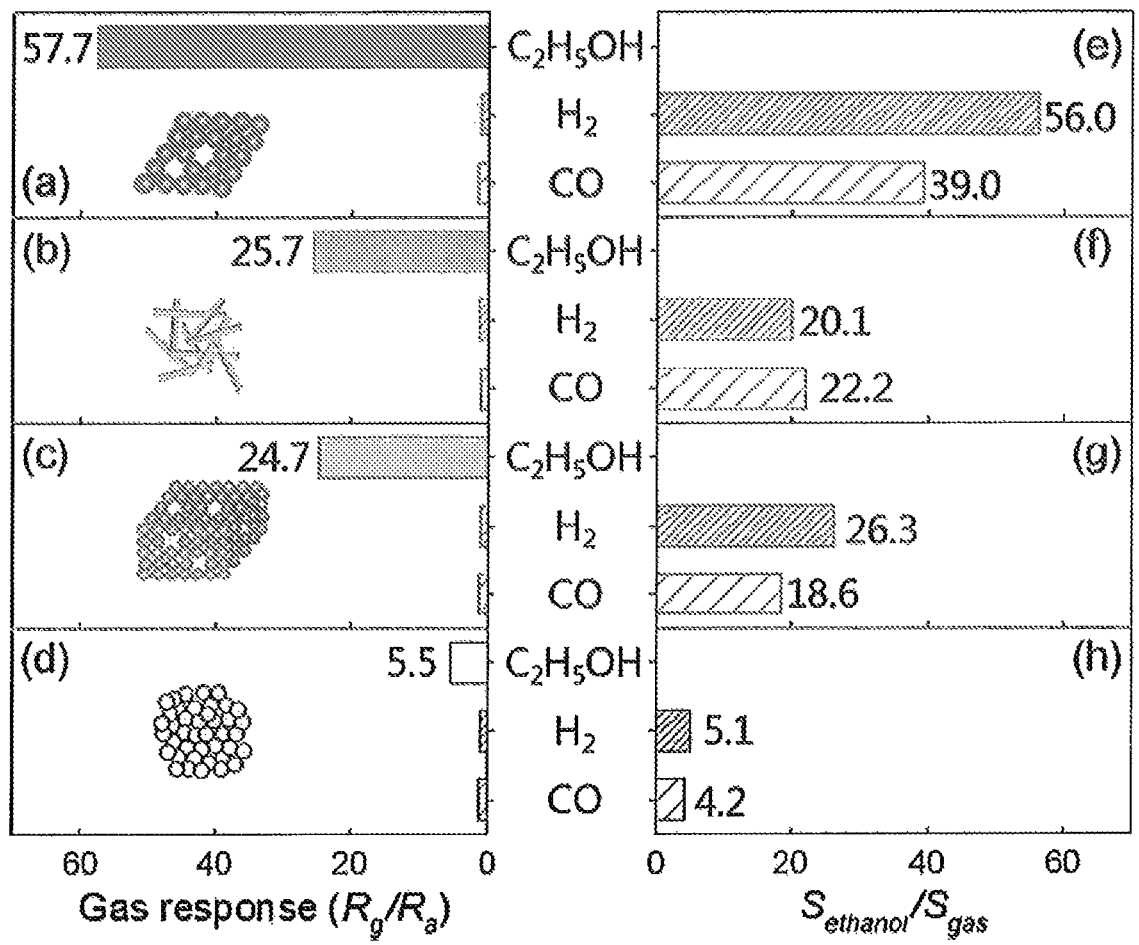
FIG. 26 includes eight graphs showing the gas response and the selectivity of the four nanostructures of cobalt oxide of FIG. 23.
Figure 27:
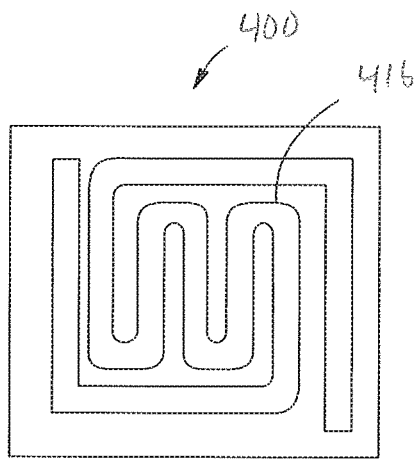
FIG. 27 is a top plan view of another embodiment of a gas sensor device having a serpentine shaped heater and gas-sensitive portions.
Figure 28:
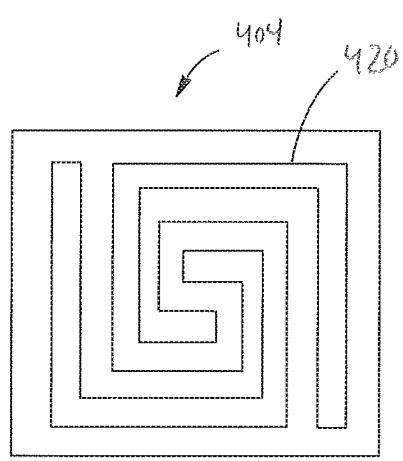
FIG. 28 is a top plan view of yet another embodiment of a gas sensor device having a serpentine shaped heater and gas-sensitive portions.
Figure 29:
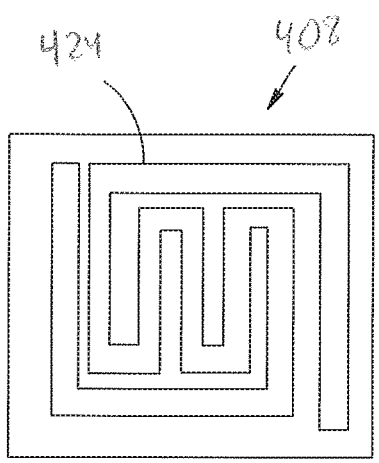
FIG. 29 is a top plan view of a further embodiment of a gas sensor device having a serpentine shaped heater and gas-sensitive portions.
Figure 30:
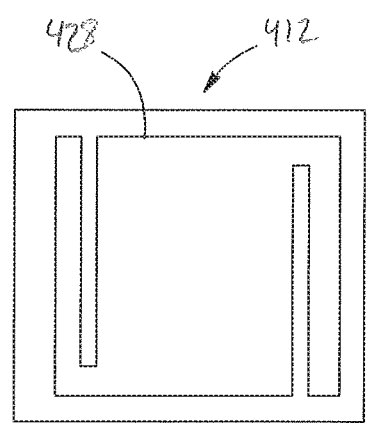
FIG. 30 is a top plan view of another embodiment of a gas sensor device having a rectangular-shaped heater and gas-sensitive portions.

In further tests it was determined that the increased surface area of ALD deposited nanostructured cobalt oxide results in a reduction in the response time of an order of magnitude above any of the nanostructures of tested in FIG. 25. Therefore, a typical response time of the ALD deposited cobalt oxide sensor layer 212 is on the order of approximately one second, making the sensor device 100 one of the fastest alcohol sensors presently available FIG. 26 illustrates the cross sensitivity of various types of nanostructured cobalt oxide by illustrating the response (left side) and the selectivity (right side) of the structures in response to hydrogen and carbon monoxide. The gas response of the structures (graphs (a), (b), (c), and (d)) is consistent with the gas response of FIG. 24. The selectivity data (graphs (e), (f), (g), and (h)) show that nanosheet cobalt oxide is the most selective to alcohol in the presence of hydrogen and carbon monoxide as compared to nanowire, nanocube, and agglomerated powder cobalt oxide.

FIGS. 22-26 show that the surface area per gram of cobalt oxide is a factor that determines the suitability of the structure as the sensing material of the sensor device 100. ALD deposited cobalt oxide results in an exceptionally high surface area per gram and, therefore, performs even better than nanosheet structure cobalt dioxide, and ALD nanostructured cobalt oxide is suitable for optimizing the sensitivity of a cobalt oxide to alcohol.

FIGS. 27-30 show four embodiments of a sensor device 400, 404, 408, 412 each of which includes a suspended sensor portion 416, 420, 424, 428. The sensor devices 400, 404, 408, 412 are identical to the sensor device 100 except that the shape of the suspended sensor portions 416, 420, 424, 428 differs from the shape of the suspended portion 122. Specifically, the suspended sensor portions 416, 420, 424 of FIGS. 17-19 illustrate a modified serpentine pattern. The suspended portion 428 of FIG. 20 is non-serpentine and defines a rectangular/square geometry that may be well suited for the receiving the nanosheet structured cobalt oxide. Specifically, in one embodiment, the suspended portion 428 defines a surface area of approximately 250 µm$^2$ for receiving the ALD deposited nanostructured cobalt oxide.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A thin film gas sensor device comprising:
   a substrate;
   a first pillar supported by the substrate;
   a second pillar supported by the substrate;
   a third pillar supported by the substrate;
   a fourth pillar supported by the substrate, the third pillar and the fourth pillar located between the first pillar and the second pillar;
   a nanostructured thin film layer extending from the first pillar, the second pillar, the third pillar, and the fourth pillar, and formed with a semi-conductor material including holes, wherein the semiconductor material is configured to undergo a reduction in a density of the holes in the presence of a target gas thereby increasing an electrical resistance of the nanostructured thin film layer, the nanostructured thin film layer including a first and a second contact portion, the first contact portion electrically connected to the first pillar and the second contact portion electrically connected to the second pillar;
   a heater layer configured to joule heat the nanostructured thin film layer to a predetermined operating temperature, the heater layer extending from the third pillar and the fourth pillar, and spaced apart from the first pillar and the second pillar, the heater layer including a third and a fourth contact portion, the third contact portion electrically connected to the third pillar and the fourth contact portion electrically connected to the fourth pillar; and
   a seed layer configured to electrically isolate the nanostructured thin film layer from the heater layer, the third pillar, and the fourth pillar,
   wherein the increase in electrical resistance is detected between the first and second contact portions,
   wherein the nanostructured thin film layer is formed using atomic layer deposition.

2. The thin film gas sensor device of claim 1, wherein:
   the nanostructured thin film layer is formed from nanostructured nickel oxide (NiO), and
   the target gas is carbon monoxide.

3. The thin film gas sensor device of claim 1, wherein:
   the nanostructured thin film layer is formed from nanostructured cobalt oxide ($Co_3O_4$), and
   the target gas is an alcohol.

4. The thin film gas sensor device of claim 1, wherein:
   the nanostructured thin film layer is formed from nanostructured nickel oxide (NiO), and
   the predetermined operating temperature is 330° C.

5. The thin film gas sensor device of claim 1, wherein:
   the nanostructured thin film layer is formed from nanostructured cobalt oxide ($Co_3O_4$), and
   the predetermined operating temperature is 400° C.

6. The thin film gas sensor device of claim 1, wherein a suspended portion of the nanostructured thin film layer is suspended above the substrate.

7. A method of fabricating a thin film gas sensor device comprising:
   providing a substrate;
   supporting a first pillar with the substrate;
   supporting a second pillar with the substrate;
   supporting a third pillar with the substrate;
   supporting a fourth pillar with the substrate, the third pillar and the fourth pillar located between the first pillar and the second pillar;
   forming a nanostructured thin film layer extending from the first pillar, the second pillar, the third pillar, and the fourth pillar using a semi-conductor material including holes, wherein the semiconductor material is configured to undergo a reduction in a density of the holes in the presence of a target gas thereby increasing an electrical resistance of the nanostructured thin film layer;
   forming a heater layer configured to joule heat the nanostructured thin film layer to a predetermined operating temperature, the heater layer extending from the third pillar and the fourth pillar, and spaced apart from the first pillar and the second pillar; and
   forming a seed layer configured to electrically isolate the nanostructured thin film layer from the heater layer, the third pillar, and the fourth pillar; and
   operably connecting a first and a second electrical contact to the nanostructured thin film layer such that the increase in electrical resistance can be detected.

8. The method of claim 7, further comprising:
   forming the nanostructured thin film layer from nickel oxide (NiO) using atomic layer deposition.

9. The method of claim 7, further comprising:
   forming the nanostructured thin film layer from cobalt oxide ($Co_3O_4$) using atomic layer deposition.

10. The method of claim 7, further comprising:
    forming a sacrificial layer above the substrate;
    forming the seed layer from a first material above the substrate; and
    forming the nanostructured thin film layer from a second material on the seed layer.

11. The method of claim 10, further comprising:
    removing the sacrificial layer to suspend a suspended portion of the seed layer and the nanostructured thin film layer above the substrate.

12. A method of using a thin film gas sensor device comprising:
    obtaining a first electrical resistance reading across a nanostructured thin film layer with the nanostructured thin film layer at a first temperature, wherein the nanostructured thin film layer includes a semi-conductor material including holes, the semiconductor material configured to undergo a reduction in a density of the holes in the presence of a target gas thereby increasing an electrical resistance of the nanostructured thin film layer;

exposing the nanostructured thin film layer to a gaseous environment after obtaining the first reading;

obtaining a second electrical resistance reading across the nanostructured thin film layer with the nanostructured thin film layer at the first temperature, after exposing the nanostructured thin film layer to the gaseous environment;

comparing the first obtained reading and the second obtained reading;

joule heating the nanostructured thin film layer to a second temperature with a heater layer prior to exposing the nanostructured thin film layer to the gaseous environment, the second temperature different from the first temperature;

obtaining a third electrical resistance reading across the nanostructured thin film layer with the nanostructured thin film layer at the second temperature prior to exposing the nanostructured thin film layer to the gaseous environment;

obtaining a fourth electrical resistance reading across the nanostructured thin film layer with the nanostructured thin film layer at the second temperature after exposing the nanostructured thin film layer to the gaseous environment;

comparing the third obtained reading and the fourth obtained reading; and determining if the target gas is present in the gaseous environment based upon the comparison of the first obtained reading and the second obtained reading and the comparison of the third obtained reading and the fourth obtained reading, wherein a first pillar, a second pillar, a third pillar, and a fourth pillar are supported by a substrate of the thin film gas sensor device, wherein the nanostructured thin film layer extends from the first pillar, the second pillar, the third pillar, and the fourth pillar, and wherein the heater layer extends from the third pillar and the fourth pillar, and the heater layer is spaced apart from the first pillar and the second pillar.

13. The method of claim 12, wherein:

the nanostructured thin film layer is formed from nickel oxide (NiO) using atomic layer deposition, and the second temperature is 330° C.

14. The method of claim 12, wherein:

the nanostructured thin film layer is formed from cobalt oxide ($Co_3O_4$) using atomic layer deposition, and the second temperature is 400° C.

* * * * *